US011841246B2

United States Patent
Murayama et al.

(10) Patent No.: US 11,841,246 B2
(45) Date of Patent: Dec. 12, 2023

(54) DEVICE HOLDING MEMBER AND DEVICE HOLDING MEMBER SET

(71) Applicant: FUNAI ELECTRIC CO., LTD., Osaka (JP)

(72) Inventors: Manabu Murayama, Osaka (JP); Naoyuki Wakabayashi, Osaka (JP); Kazuhiro Takahashi, Osaka (JP); Shingo Hamada, Osaka (JP)

(73) Assignee: FUNAI ELECTRIC CO., LTD., Osaka (JP)

( * ) Notice: Subject to any disclaimer, the term of this patent is extended or adjusted under 35 U.S.C. 154(b) by 354 days.

(21) Appl. No.: 17/402,586

(22) Filed: Aug. 15, 2021

(65) Prior Publication Data

US 2022/0082414 A1 Mar. 17, 2022

(30) Foreign Application Priority Data

Sep. 11, 2020 (JP) ................................. 2020-152900

(51) Int. Cl.
*G01D 11/30* (2006.01)
*G01D 11/24* (2006.01)

(52) U.S. Cl.
CPC ........... *G01D 11/30* (2013.01); *G01D 11/245* (2013.01)

(58) Field of Classification Search
CPC .............................. G01D 11/30; G01D 11/245
See application file for complete search history.

(56) References Cited

FOREIGN PATENT DOCUMENTS

| EP | 3967216 A1 | * | 3/2022 | ........... G01D 11/245 |
| JP | 2017131581 A | * | 8/2017 | |
| JP | 2017131582 | | 8/2017 | |
| JP | 2017131582 A | * | 8/2017 | |

* cited by examiner

Primary Examiner — Jamel E Williams
(74) Attorney, Agent, or Firm — JCIPRNET

(57) ABSTRACT

The disclosure provides a device holding member and a device holding member set. The device holding member is engaged with a bottom member formed with a hole or a frame supporting the bottom member and holds a device arranged on the bottom member. The device holding member includes a belt and a locking member. The belt includes an end part provided with an engaging member engageable with an edge part of the bottom member or the frame and holds the device. The locking member is provided between the engaging member and the device and locks a part of the belt to the hole.

14 Claims, 18 Drawing Sheets

DEVICE HOLDING MEMBER AND DEVICE HOLDING MEMBER SET

CROSS-REFERENCE TO RELATED APPLICATION

This application claims the priority benefit of Japan application serial no. 2020-152900, filed on Sep. 11, 2020. The entirety of the above-mentioned patent application is hereby incorporated by reference herein and made a part of this specification.

BACKGROUND

Technical Field

The disclosure relates to a device holding member and a device holding member set.

Description of Related Art

Detection devices are used to detect leaving the bed of a bed-resting person and detect biometric information such as a heartbeat, a pulse, and respiration of the bed-resting person. Such detection devices are generally arranged between a bottom member of the bed used by the bed-resting person and a mattress provided on the bottom member. In addition, the bed used by a bed-resting person may be provided with functions (so-called raising functions) such as back raising and foot raising. In such a bed, the positional relationship between the bottom member and the mattress changes due to back raising or foot raising of the raising function. As a result, the position of the detection device clamped between the bottom member and the mattress may deviate with respect to the bed-resting person.

To keep the positional relationship between the bed-resting person and the detection device constant, a member for fixing a radio wave sensor by using a penetration part (through-hole) formed in a bottom member for the purpose of ventilation or weight reduction is known (see, for example, Patent Document 1: Japanese Patent Application Laid-Open No. 2017-131582). Patent Document 1 discloses a sensor unit including two hooks, a holding member slidably holds the two hooks, and a radio wave sensor attached to the holding member and inserted from above into the penetration part (through-hole) of the bottom member.

However, in the sensor unit of Patent Document 1, since the radio wave sensor is arranged inside the penetration part (through-hole) of the bottom member, the radio wave sensor cannot be arranged at a position which is not provided with a penetration part (through-hole), and a radio wave sensor having a size larger than the size of the penetration part (through-hole) cannot be arranged. Therefore, it is desired that the radio wave sensor (device) can be arranged on a desired base such as a bottom member while suppressing restrictions on the arrangement position of the device and the size of the device, and that a position deviation of the device can be suppressed.

The disclosure provides a device holding member and a device holding member set in which a device can be arranged on a base while suppressing restrictions on the arrangement position of the device and the size of the device, and meanwhile, a position deviation of the device can be suppressed.

SUMMARY

A device holding member according to a first aspect of the disclosure is engaged with a base formed with a hole or a frame supporting the base and holds a device arranged on the base. The device holding member includes a belt and a locking member. The belt includes an end part provided with an engaging member engageable with an edge part of the base or the frame and holds the device. The locking member is provided between the engaging member and the device and locks a part of the belt to the hole.

As described above, the device holding member according to the first aspect of the disclosure includes the locking member which locks a part of the belt holding the device to the hole formed in the base. With this configuration, since a part of the belt holding the device is locked to the hole formed in the base, the device can be fixed on the base by the locked belt. Therefore, since the arrangement position of the device is not limited to, for example, inside of the hole formed in the base, the device may be arranged on the base at a position other than in the hole. Further, since the device is not arranged in the hole formed in the base, a device having a size larger than the size of the hole may be arranged on the base. As a result, it is possible to arrange the device on the base while suppressing restrictions on the arrangement position of the device and the size of the device. Further, the belt includes an end part provided with the engaging member engageable with the edge part of the base or the frame. Accordingly, since the engaging member can be engaged with the edge part of the base or the frame, the device held by the belt can be arranged at a desired position on the base. Further, the belt is not only engaged with the edge part of the base or the frame by the engaging member, but the belt is also locked to the hole of the base by the locking member. Accordingly, the belt can be locked more firmly than when the belt is engaged only by the engaging member. Therefore, it is possible to suppress a position deviation of the device resulting from an external force generated on the base. As a result, it is possible to arrange the device on the base while suppressing restrictions on the arrangement position of the device and the size of the device, and meanwhile, it is also possible to suppress a position deviation of the device.

In the device holding member according to the first aspect of the disclosure, the locking member may be configured to be inserted into the hole from a side of a surface in one direction of the base to a side of a surface in another direction of the base to lock a part of the belt to the hole. With this configuration, since the belt contacts (abuts against) the edge part of the hole in a bent state at a portion where the edge part of a surface in one direction of the hole of the base and a surface in another direction of the belt are in contact with each other, a large frictional force is generated at the contact portion. Due to the frictional force, the belt can be appropriately fixed to the hole without deviation. Therefore, it is possible to appropriately suppress a position deviation of the device resulting from an external force generated on the base.

In this case, the locking member may be configured to lock a part of the belt on the surface in the another direction of the base by inserting into the hole together with the part of the belt. In this configuration, with the locking member preventing the belt from coming off from the hole, the belt inserted into the hole can be fixed more appropriately.

In the configuration in which the locking member locks a part of the belt on the surface in the another direction of the base, the locking member may be configured to include a plate-shaped member or a rod-shaped member having an elongated shape, and the locking member may be engaged with the base by arranging a long direction of the locking member toward a short direction of the hole on the surface in the another direction of the base to be capable of preventing coming off from the hole together with the belt. With this configuration, by having the locking member pulled against the surface in the another direction of the base, the locking member can be appropriately fixed to the hole. Therefore, the belt inserted into the hole together with the locking member can be more appropriately fixed.

In the device holding member according to the first aspect of the disclosure, the locking member may be configured to include a rotating part which is rotatable and has a plate-shaped member or a rod-shaped member having an elongated shape, and in a state in which the rotating part inserted into the hole from a side of a surface in one direction of the base with a long direction of the locking member extending along a long direction of the hole is rotated toward a short direction of the hole on a surface in another direction of the base, a part of the rotating part may be engaged with the base. With this configuration, by rotating the rotating part inserted into the hole, the locking member can be easily abutted against the surface in the another direction of the base. Therefore, the belt inserted into the hole together with the locking member can be more appropriately fixed.

In the device holding member according to the first aspect of the disclosure, the locking member may be configured to include a clipping part which clips a part of the belt and a rotating part which has a plate-shaped member or a rod-shaped member having an elongated shape and is rotatable with respect to the clipping part, and in a state in which the rotating part inserted into the hole from a side of a surface in one direction of the base with a long direction of the locking member extending along a long direction of the hole is rotated toward a short direction of the hole on a surface in another direction of the base, a part of the rotating part may be engaged with the base. With this configuration, by rotating the rotating part inserted into the hole, the locking member can be easily abutted against the surface in the another direction of the base. Therefore, the belt inserted into the hole together with the locking member can be more appropriately fixed.

In the configuration of engaging with the base by arranging the locking member toward the short direction of the hole on the surface in the another direction of the base, or alternatively, in the configuration of engaging with the base with the rotating part rotated toward the short direction of the hole on the surface in the another direction of the base, the plate-shaped member or the rod-shaped member of the locking member may be configured to have a rectangular shape having a long edge and a short edge in a plan view. With this configuration, the two end parts of the long direction of the plate-shaped member or the rod-shaped member of the locking member can be easily engaged with the surface in the another direction of the base.

In the configuration of engaging with the base by arranging the locking member toward the short direction of the hole on the surface in the another direction of the base, or alternatively, in the configuration of engaging with the base with the rotating part rotated toward the short direction of the hole on the surface in the another direction of the base, the plate-shaped member or the rod-shaped member of the locking member may be configured to include a pair of long edges and notched parts cut out respectively at the pair of long edges in a plan view, and with the locking member engaged with the base on the surface in the another direction of the base, a part of the belt may be arranged in the notched part. With this configuration, the two end parts of the long direction of the plate-shaped member or the rod-shaped member of the locking member and the surface in the another direction of the base can be appropriately engaged with each other, and in the notched part, a part of the belt can also be locked by the notched part and the base.

In the configuration in which the locking member locks a part of the belt on the surface in the another direction of the base, the locking member may be configured to include a pair of sidewalls and a bottom part connecting the pair of sidewalls, and by restoring the pair of sidewalls which has been inserted into the hole from a side of the bottom part with the pair of sidewalls elastically deformed in a direction approaching each other, the locking member may be capable of preventing coming off from the hole together with the belt. With this configuration, the locking member can be easily inserted into the hole from the side of a surface in one direction of the base, and the restored locking member and the base can be easily engaged with each other. Therefore, the belt inserted into the hole together with the locking member can be more appropriately fixed.

In the device holding member according to the first aspect of the disclosure, the locking member may be configured to include a pair of sidewalls and a bottom part connecting the pair of sidewalls, the pair of sidewalls may include a pair of wall parts connected to the bottom part, and at least one pair of protruding parts protruding from the pair of wall parts toward an outer side of the pair of wall parts, and with restoration of the pair of sidewalls which has been inserted into the hole from a side of the bottom part with the pair of sidewalls elastically deformed in a direction approaching each other, the pair of protruding parts may be engaged with end parts of the hole. With this configuration, the locking member can be easily inserted into the hole from the side of a surface in one direction of the base, and the pair of protruding parts of the restored locking member and the base can also be easily engaged with each other. Therefore, the belt inserted into the hole together with the locking member can be more appropriately fixed.

In the device holding member according to the first aspect of the disclosure, the belt may be composed of a pair of belt parts connected to one side and another side of the device, and each of the pair of belt parts may include the engaging member, a connecting part connectable with the device, and a belt main body part which connects the engaging member and the connecting part. In this configuration, with the connecting parts of the pair of belt parts, the device can be appropriately held from one side and another side of the device even at a position where the hole is not provided.

In this case, a length of the belt may be configured to be adjustable by at least one of the engaging member, the connecting part, and the belt main body part. With this configuration, since the length of the belt can be adjusted by any of the engaging member, the connecting part, and the belt main body part, a tension can be applied to the belt main body part between the engaging member and the device. Accordingly, the locking member and the base can be appropriately abutted against each other. Therefore, the belt inserted into the hole together with the locking member can be fixed more appropriately.

A device holding member set according to a second aspect of the disclosure includes a rotation assisting tool and a device holding member which is engaged with a base formed with a hole or a frame supporting the base and holds a device arranged on the base. The device holding member includes a belt and a locking member. The belt holds the device and includes an end part provided with an engaging member engageable with an edge part of the base or the frame. The locking member is provided between the engaging member and the device and locks a part of the belt to the hole. The locking member includes a rotating part which is rotatable and has a plate-shaped member or a rod-shaped member having an elongated shape. In a state in which the rotating part inserted into the hole from a side of a surface in one direction of the base with a long direction of the locking member extending along a long direction of the hole is rotated toward a short direction of the hole on a surface in another direction of the base, a part of the rotating part is engaged with the base. The rotating part includes multiple recesses arranged on one surface on one side and another side of a rotation center axis. The rotation assisting tool includes multiple protrusions provided in correspondence to the recesses of the rotating part.

In the device holding member set according to the second aspect of the disclosure, as described above, the end part provided with the engaging member engageable with the edge part of the base or the frame is provided, and the locking member which locks a part of the belt holding the device to the hole formed in the base is included. With this configuration, similar to the first aspect, it is possible to arrange the device on the base while suppressing restrictions on the arrangement position of the device and the size of the device, and meanwhile, it is also possible to suppress a position deviation of the device resulting from an external force generated on the base. Further, the rotating part includes multiple recesses arranged on one surface on one side and another side of the rotation center axis, and the rotation assisting tool includes multiple protrusions provided in correspondence to the recesses of the rotating part. With this configuration, the rotating part can be rotated by the rotation assisting tool.

In the device holding member set according to the second aspect of the disclosure, with the protrusions of the rotation assisting tool inserted into the recesses of the rotating part, the rotating part may be configured to be rotatable by rotating the rotation assisting tool around the rotation center axis. With this configuration, the rotating part can be easily rotated by the rotation assisting tool.

DESCRIPTION OF THE EMBODIMENTS

Figure 1:
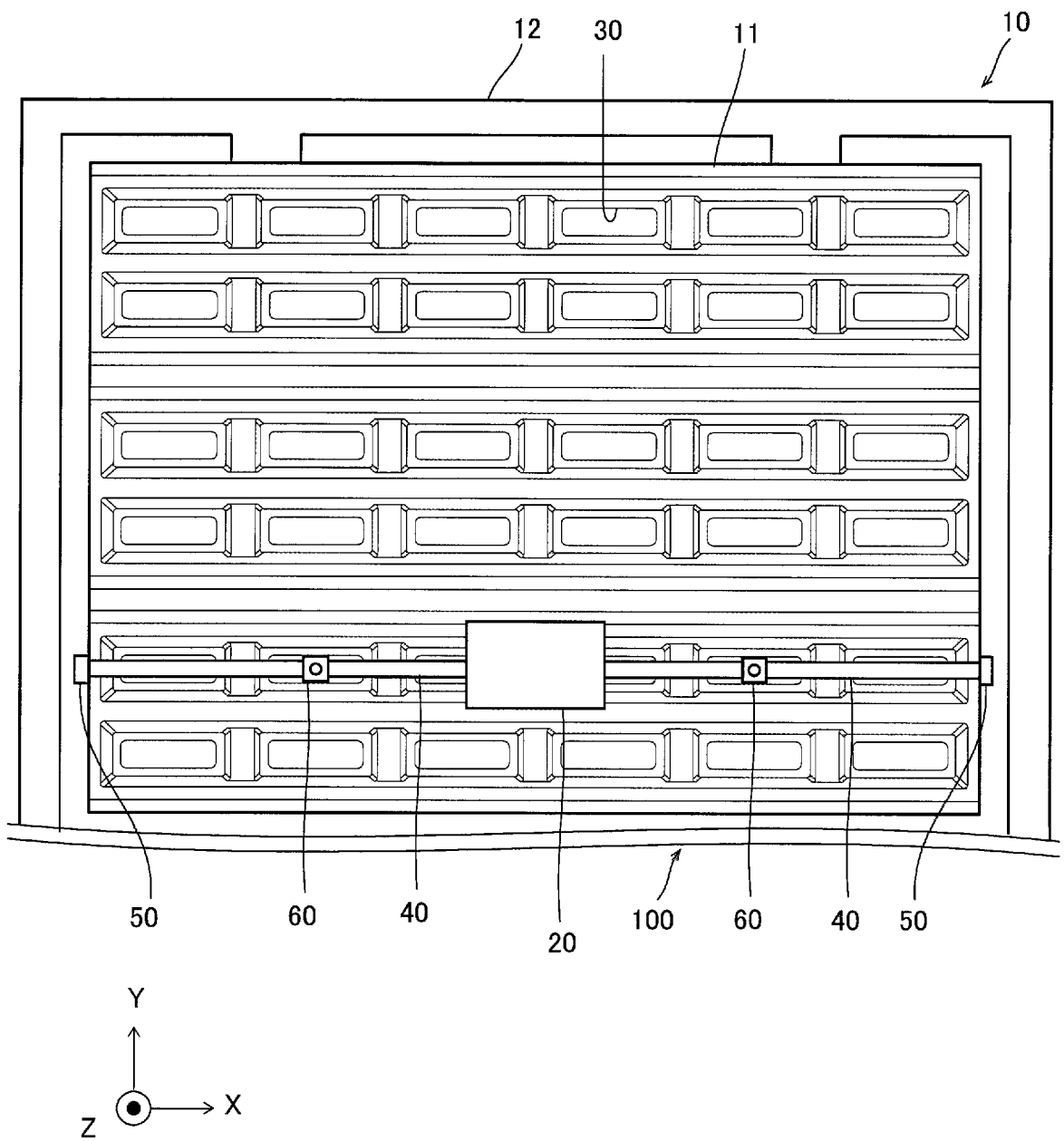
FIG. 1 is a schematic plan view of a bed to which a device holding member according to a first embodiment is attached.

According to the disclosure, it is possible to provide a device holding member and a device holding member set in which a device can be arranged on a base while suppressing restrictions on the arrangement position of the device and the size of the device, and meanwhile, a position deviation of the device can be suppressed.

First Embodiment (Configuration of Bed to which Device Holding Member is Attached)

Referring to FIG. 1 to FIG. 5, configurations of a device holding member 100 according to a first embodiment and a bed 10 which is attached with the device holding member 100 and includes a bottom member 11 and a frame 12 will be described. In this specification, the left-right direction (the short direction of the bed 10) of a bed-resting person lying on a mattress on the bed 10 will be described as a left-right direction (X direction). Further, the head-foot direction (the long direction of the bed 10) of the bed-resting person lying on the mattress on the bed 10 will be described as a front-rear direction (Y direction). Further, the vertical direction of the bed will be described as an up-down direction (Z direction). The bottom member 11 is an example of a "base" of the claims.

As shown in FIG. 1, the bed 10 to which the device holding member 100 is attached includes a bottom member 11 on which a mattress (not shown) is placed, a frame 12 which supports the bottom member 11, and an adjustment device (not shown) for executing a raising function by adjusting the inclination of the bottom member 11 on the lower side of the bottom member 11. Although not shown, the bottom member 11 is configured to be divided to respectively correspond to parts of the bed-resting person such as the back part, the waist part, and the foot part. However, the adjustment device does not have to be arranged on the lower side of the bottom member 11.

Figure 2:
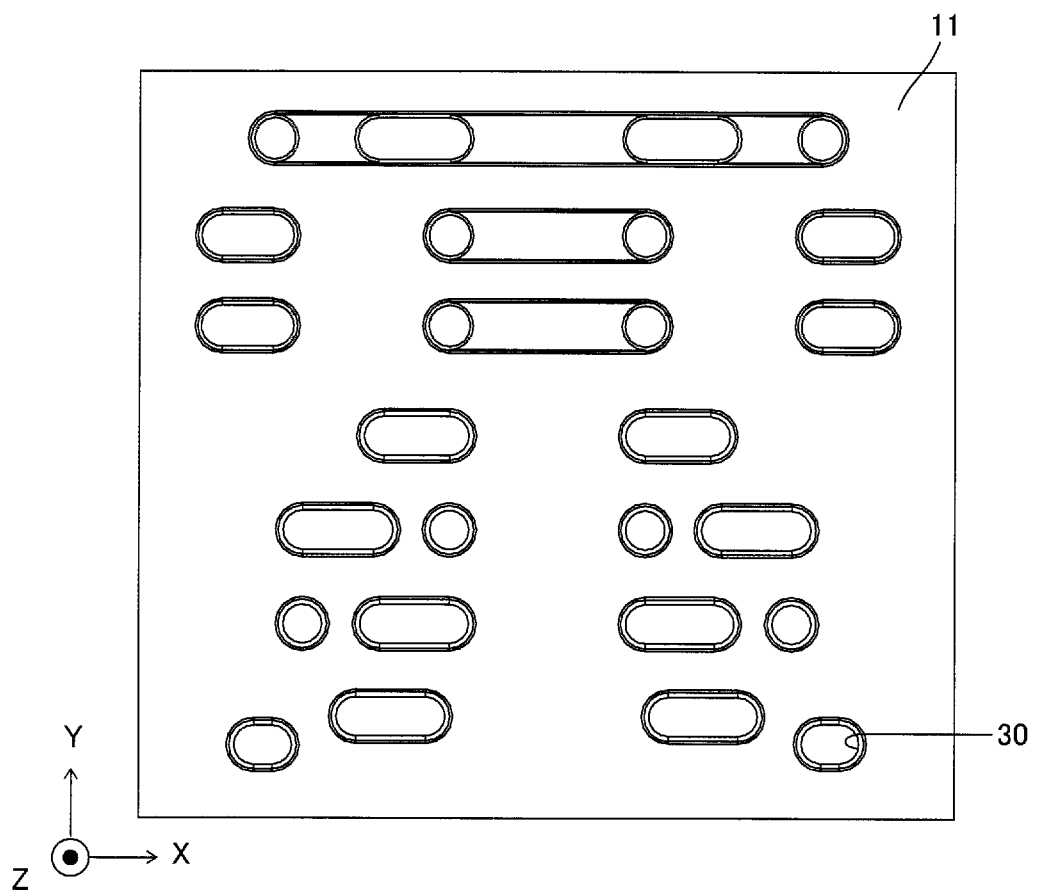
FIG. 2 is a schematic view showing Example 1 of a hole formed in a bottom member according to the first embodiment.
Figure 3:
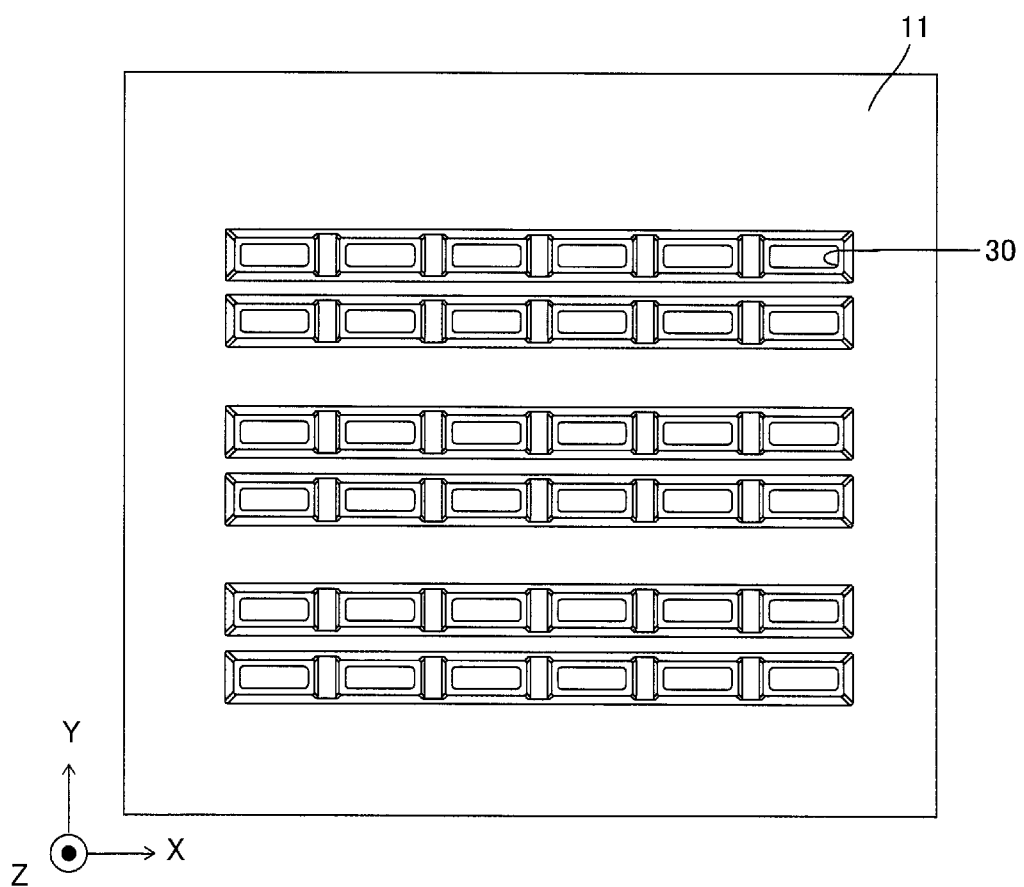
FIG. 3 is a schematic view showing Example 2 of the hole formed in the bottom member according to the first embodiment.

The bottom member 11 is formed with multiple holes 30 to increase air permeability of the mattress provided on the upper side of the bottom member 11 or to reduce the weight. As shown in FIG. 2 and FIG. 3, the arrangement of the holes 30 formed in the bottom member 11 includes multiple variations. Further, the shape of the holes 30 formed in the bottom member 11 also includes multiple variations. In the first embodiment, the holes 30 formed in the bottom member 11 have a rectangular or elliptical shape having a long edge (long axis) and a short edge (short axis) in a plan view. The holes 30 are formed along the left-right direction of the bed 10. The holes 30 are arranged so that the long edge of the hole 30 extends along the left-right direction of the bed 10.

(Configuration of Device Holding Member)

Figure 4:
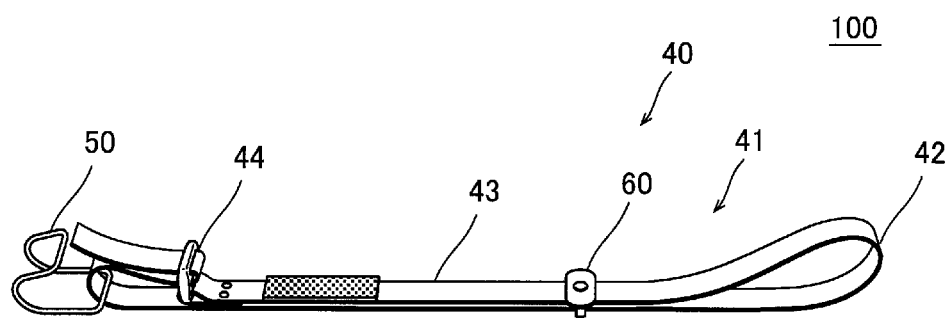
FIG. 4 is a schematic view of a belt part of the device holding member according to the first embodiment.

As shown in FIG. 1 and FIG. 4, the device holding member 100 according to the first embodiment includes a belt 40 and a locking member 60. The belt 40 is composed of a pair of belt parts 41 (see FIG. 4) connected to one side and the other side in the left-right direction of a device 20 (see FIG. 1). The belt part 41 includes an engaging member 50 engageable with the bottom member 11, a connecting part 42 connectable with the device 20, and a belt main body part 43 which connects the engaging member 50 and the connecting part 42. Although FIG. 4 shows one of the pair of belt parts 41, it is understood that the other belt part 41 has the same configuration.

Figure 5:
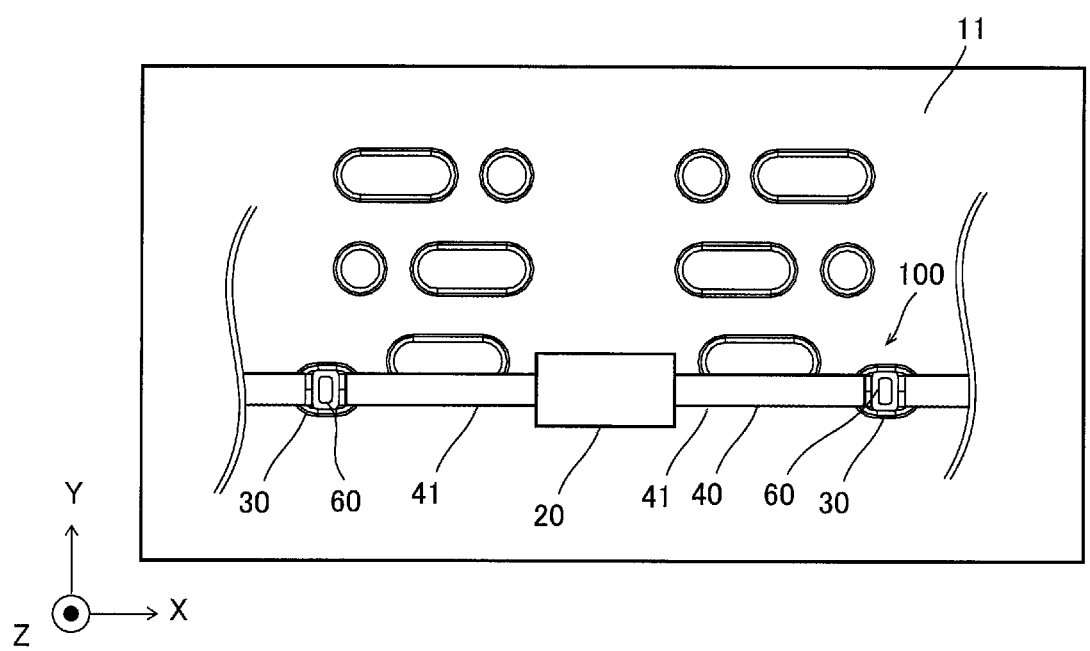
FIG. 5 is a schematic view showing an example in which the device holding member according to the first embodiment is attached to the bottom member.

As shown in FIG. 5, in the device holding member 100, the belt 40 including the pair of belt parts 41 is arranged on the bottom member 11 along the left-right direction of the bottom member 11, and the locking member 60 locks the belt 40 to the holes 30 in left and right directions of the device. It is also possible that the extending direction of the belt 40 is not the left-right direction (X direction) of the bottom member 11, but may be, for example, the front-rear direction (Y direction) of the bottom member 11.

The device 20 (see FIG. 1) includes, for example, a sensor for acquiring biometric information of a bed-resting person who uses the bed 10. Examples of the sensor include a sensor for detecting leaving the bed of the bed-resting person and a sensor for detecting body motions such as a heartbeat, a pulse, or respiration of the bed-resting person. The device 20 is not limited to a sensor for acquiring biometric information of the bed-resting person, but may also be, for example, a device for assisting with care and treatment of the bed-resting person. Each of the side surfaces in the left-right direction of the device 20 is provided with an insertion hole (not shown) formed to be connectable with the belt part 41 by inserting and folding back the belt main body part 43.

Figure 6:
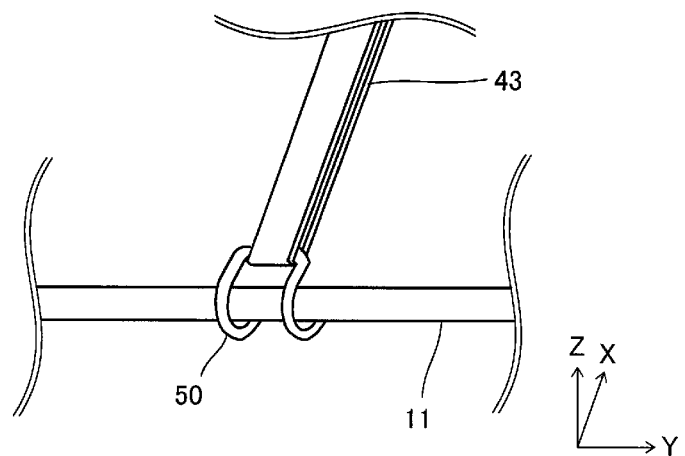
FIG. 6 is a schematic view showing an example in which an engaging member according to the first embodiment is attached to the bottom member.
Figure 7:
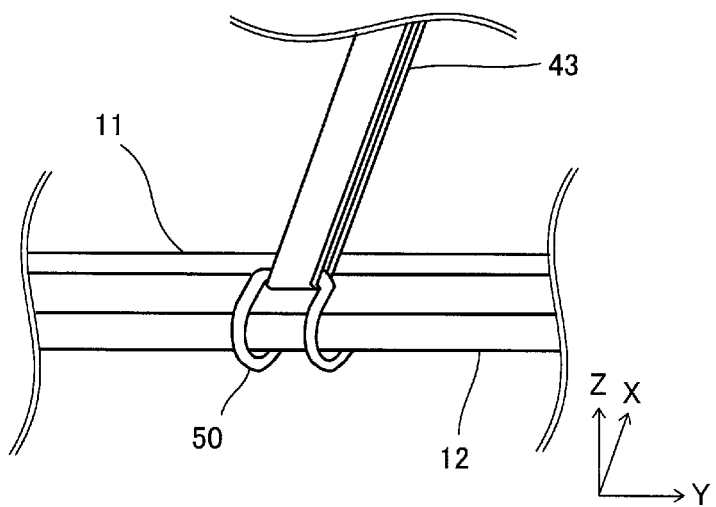
FIG. 7 is a schematic view showing an example in which the engaging member according to the first embodiment is attached to a frame.

As shown in FIG. 4, the engaging member 50 is, for example, a hook. As shown in FIG. 6, the hook serving as the engaging member 50 is configured to be engageable with the bottom member 11 by hooking to a peripheral part in the left-right direction of the bottom member 11. Also, for example, when the bottom member 11 and a part of the frame 12 integrally perform back raising or foot raising, as shown in FIG. 7, the engaging member 50 may be engaged with a peripheral part in the left-right direction of a part of the frame 12.

The connecting part 42 is configured to hold the device 20 by folding back the belt main body part 43, which is formed of a band-shaped member, in the insertion hole provided at the device 20.

The belt main body part 43 connects the engaging member 50 and the connecting part 42. The belt main body part 43 has a band shape. The belt main body part 43 is formed of a non-stretchable material. The belt main body part 43 is provided with an adjuster 44 capable of adjusting the length of the belt main body part 43. The adjuster 44 is, for example, a slider adjuster.

Figure 8:
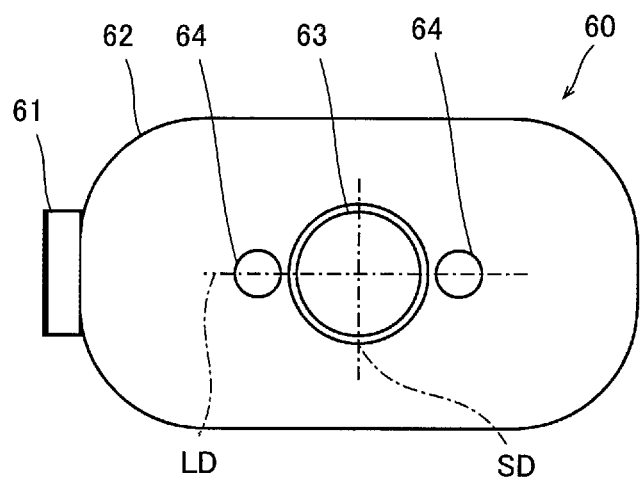
FIG. 8 is a schematic plan view of a locking member according to the first embodiment.
Figure 9:
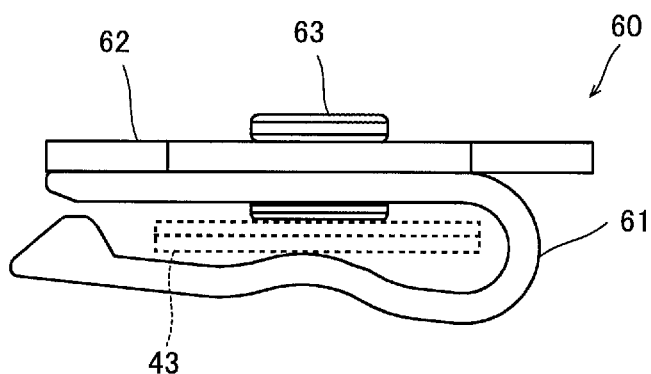
FIG. 9 is a schematic front view of the locking member according to the first embodiment.
Figure 10:
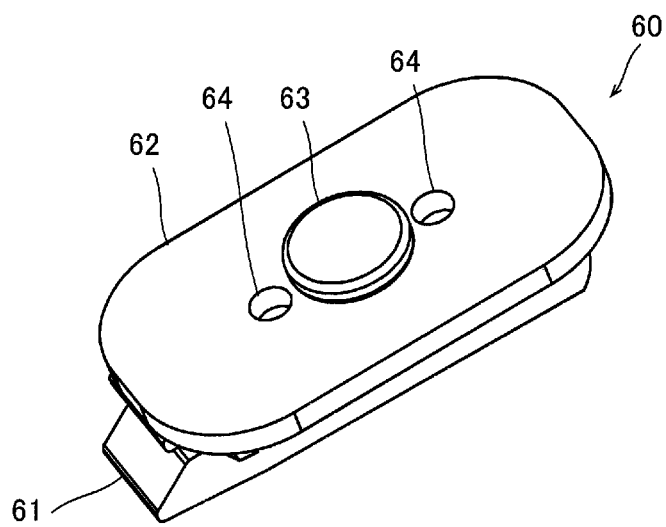
FIG. 10 is a perspective view of the locking member according to the first embodiment.

As shown in FIG. 5, the locking member 60 is configured to lock a part of the belt main body part 43 (see FIG. 4) to the hole 30 formed in the bottom member 11. As shown in FIG. 8 to FIG. 10, the locking member 60 includes a clipping part 61, a rotating part 62, and a shaft part 63 connecting the clipping part 61 and the rotating part 62. The locking member 60 is detachably provided on the belt main body part 43 (see FIG. 9) between the engaging member 50 and the device 20. The locking member 60 is configured to lock a part of the belt main body part 43 to the hole 30 formed in the bottom member 11. The method of locking the belt main body part 43 to the hole 30 by the locking member 60 will be described later.

The clipping part 61 clips a part of the belt main body part 43 (see FIG. 9). The clipping part 61 is configured to be detachable with respect to the belt main body part 43. The clipping part 61 is, for example, a clip. The clip serving as the clipping part 61 is composed of a pair of elongated plate-shaped members of which one-side ends are connected to each other. By inserting the belt main body part 43 from between other-side ends of the plate-shaped members toward the one-side ends, the clipping part 61 clips a part of the belt main body part 43 with the belt main body part 43 inserted through it.

The rotating part 62 is composed of a plate-shaped member or a rod-shaped member. In a plan view, the plate-shaped member serving as the rotating part 62 is formed in an elongated shape having a polygonal shape having a long part and a short part or an elliptical shape having a long diameter and a short diameter. The long part or the long diameter in the rotating part 62 is smaller than the long edge of the hole 30 to which the locking member 60 is locked and larger than the short edge of the hole 30. In the first embodiment, the rotating part 62 is a rectangular plate-shaped member having a long edge and a short edge in a plan view. The rotating part 62 is configured to be rotatable on the axis of the shaft part 63 with respect to the clipping part 61. Hereinafter, the long direction (long axis) of the rotating part 62 is labeled as LD, and the short direction (short axis) of the rotating part 62 is labeled as SD.

Multiple recesses 64 provided on one side and the other side of the shaft part 63 are formed on the upper surface of the rotating part 62. In the first embodiment, two recesses 64 are formed.

The shaft part 63 is configured to connect the clipping part 61 and the rotating part 62 and may rotate the rotating part 62 on the axis of the shaft part 63 with respect to the clipping part 61. The shaft part 63 is, for example, a rivet.

(Configuration of Rotation Assisting Tool)

Figure 11:
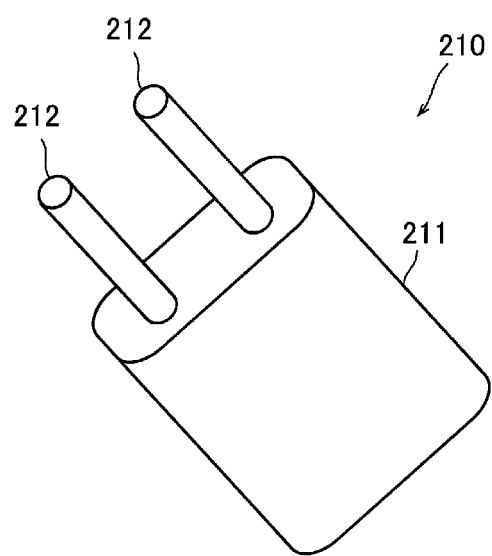
FIG. 11 is a perspective view of a rotation assisting tool according to the first embodiment.

With the locking member 60 mounted to the belt main body part 43, the rotating part 62 may be rotated by using a rotation assisting tool 210 shown in FIG. 11. The rotation assisting tool 210 includes a grip part 211 having a rectangular parallelepiped shape which may be gripped by the fingers of a hand, and multiple protrusions 212 provided on one surface of the grip part 211 in correspondence to the arrangement and the depth of the recesses 64 of the rotating part 62. The rotation assisting tool 210 is configured to be capable of rotating the rotating part 62 by rotating on the axis of the shaft part 63 with the protrusions 212 inserted into the recesses 64 of the rotating part 62. The rotation assisting tool 210 and the device holding member 100 form a device holding member set.

(Method of Locking Belt Main Body Part by Locking Member)

Figure 12:
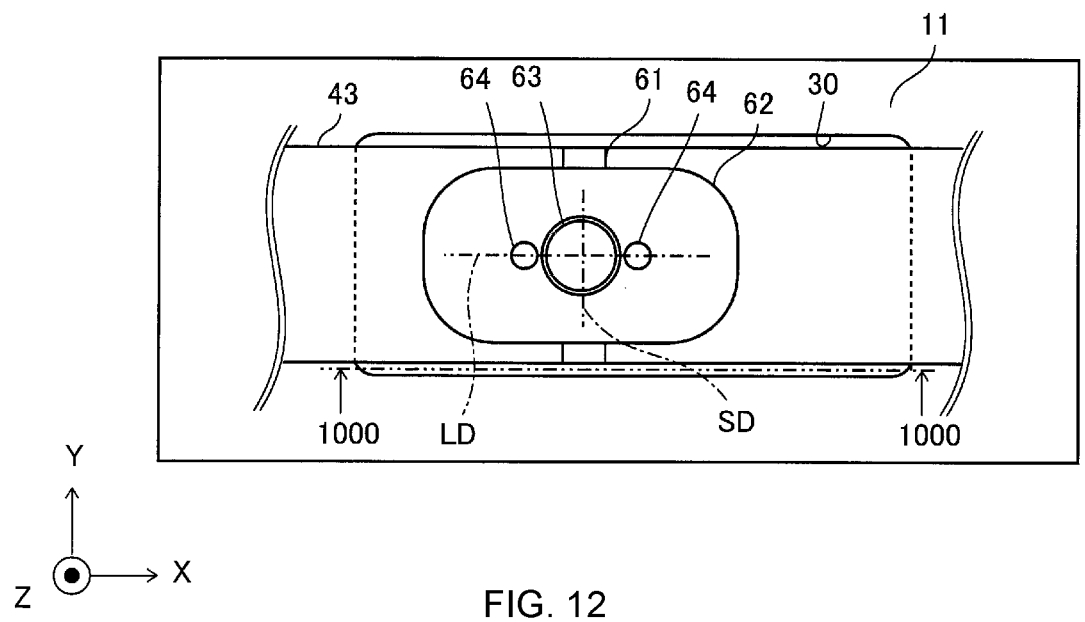
FIG. 12 is a first view showing a locking method by the locking member according to the first embodiment.
Figure 13:
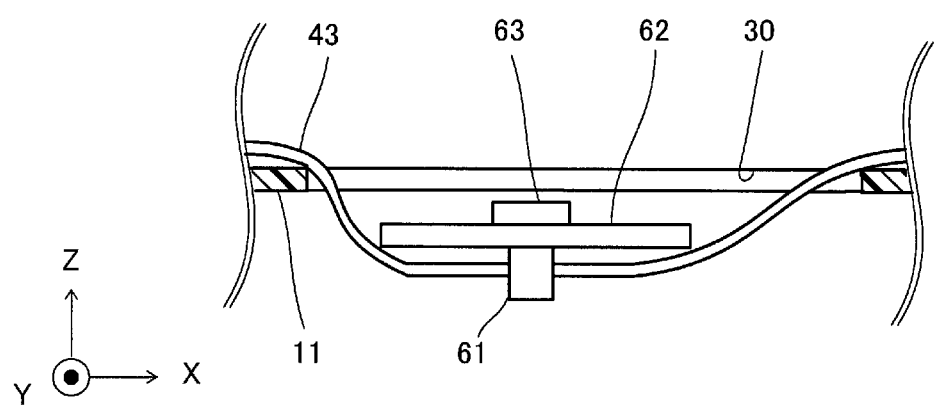
FIG. 13 is a cross-sectional view taken along line 1000-1000 in FIG. 10.
Figure 14:
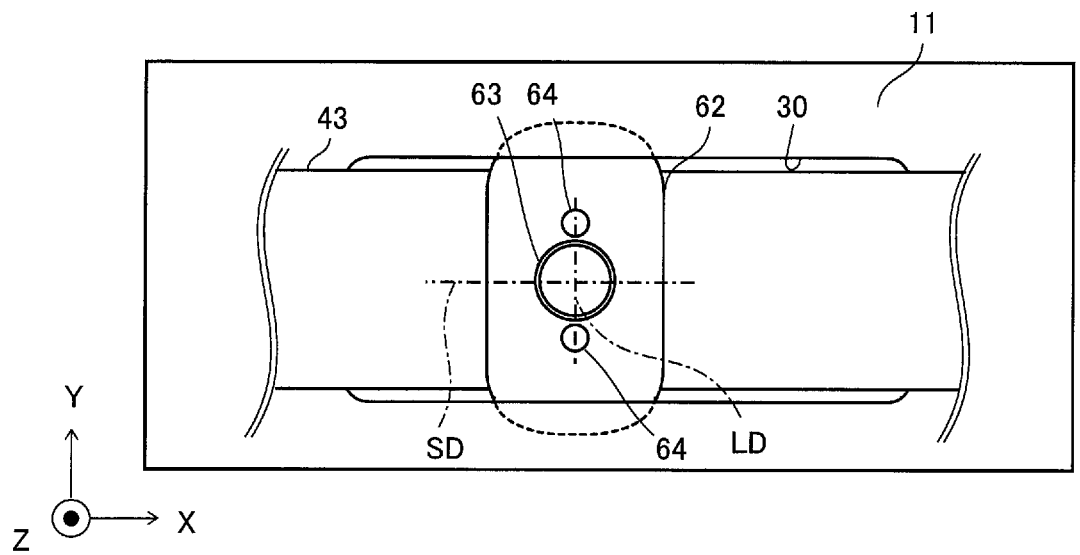
FIG. 14 is a second view showing the locking method by the locking member according to the first embodiment.

Referring to FIG. 12 to FIG. 14, a method of locking the belt main body part 43 by the locking member 60 according to the first embodiment will be described.

FIG. 12 is a schematic view showing a state in which the locking member 60 is inserted into the hole 30 formed in the bottom member 11 as viewed from the upper surface side of the bottom member 11. As shown in FIG. 12, the belt main body part 43 is placed so that the long direction of the belt main body part 43 extends along the long direction (X direction) of the hole 30 and the belt main body part 43 passes over the hole 30. The clipping part 61 clips the belt main body part 43. The rotating part 62 is arranged to be accommodated in the hole 30 with the long direction LD of the rotating part 62 extending along the long direction (X direction) of the hole 30. The locking member 60 is inserted together with a part of the belt main body part 43 into the hole 30 from the upper surface side of the bottom member 11 toward the lower surface side of the bottom member 11. As shown in FIG. 13, in the hole 30, the upper surface of the rotating part 62 is inserted to be located lower than the lower surface of the bottom member 11.

Figure 15:
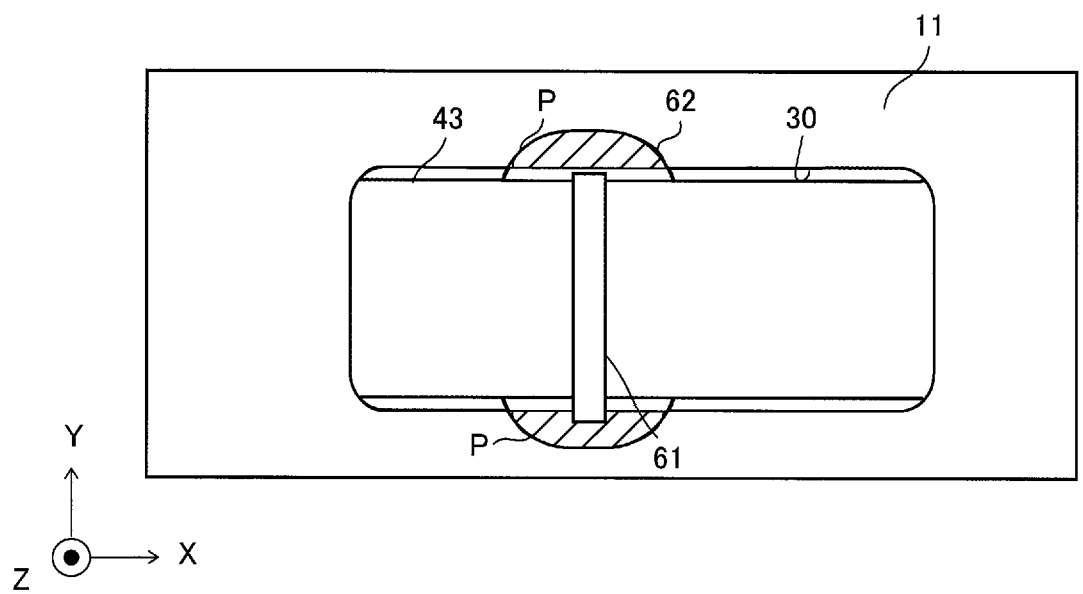
FIG. 15 is a third view showing the locking method by the locking member according to the first embodiment.

FIG. 14 is a schematic view showing a state in which the rotating part 62 of FIG. 12 is rotated as viewed from the upper surface side of the bottom member 11. FIG. 15 is a schematic view showing a state in which the rotating part 62 of FIG. 12 is rotated as viewed from the lower surface side of the bottom member 11. FIG. 14 and FIG. 15 show a state in which the rotating part 62 inserted into the hole with the long direction LD of the locking member 60 extending along the long direction (X direction) of the hole 30 as shown in FIG. 12 is rotated by 90 degrees toward the short direction (Y direction) of the hole 30 on the lower surface of the bottom member 11. In other words, the locking member 60 inserted into the hole 30 with the long direction LD of the locking member 60 extending along the long direction (X direction) of the hole 30 is arranged to be tilted by 90 degrees toward the short direction (Y direction) of the hole 30 on the lower surface of the bottom member 11, and the short direction SD of the locking member 60 changes to extend along the long direction (X direction) of the hole 30. The rotation of the rotating part 62 is performed by using the rotation assisting tool 210.

After the rotating part 62 is rotated, by adjusting the adjuster 44 of the belt part 41 to apply a tension to the belt main body part 43 between the engaging member 50 and the device 20, as shown in FIG. 14 and FIG. 15, the upper surface at a vicinity P (hatched portion in FIG. 15) near two end parts of the long direction LD of the rotating part 62 abuts against the lower surface of the bottom member 11. Accordingly, by having the vicinity P of the two end parts of the long direction LD of the rotating part 62 pulled against the lower surface of the bottom member 11, the rotating part 62 and the bottom member 11 are engaged with each other, and as a result, the locking member 60 prevents coming off from the hole together with the belt main body part 43. In addition, with the upper surface at the vicinity P of the two end parts of the long direction LD of the rotating part 62 abutted against the lower surface of the bottom member 11, two end parts along the long direction LD of the rotating part 62 and the belt main body part 43 abut against each other, and the bottom member 11 on the short edge side of the hole 30 and the belt main body part 43 abut against each other. Accordingly, a frictional force is generated between the two end parts along the long direction LD of the rotating part 62 and the belt main body part 43 that abuts against these two end parts, and a frictional force is also generated between the bottom member 11 on the short edge side of the hole 30 and the belt main body part 43 that abuts against the bottom member 11. Therefore, the belt main body part 43 is less likely to deviate with respect to the hole 30, and as a result, the belt main body part 43 is locked to the hole 30.

As it is only necessary that the locking member 60 can pass through the hole 30 from the upper surface side of the bottom member 11 to the lower surface side of the bottom member 11, the long direction and the short direction of the hole 30 may extend along any direction in the bottom member 11. Further, the width of the rotating part 62 may be larger than the width of the hole 30.

A method of releasing locking of the belt main body part 43 to the hole 30 by the locking member 60 and removing the locking member 60 from the hole 30 will be described. With a part of the belt main body part 43 locked to the hole 30 by the locking member 60, the adjuster 44 of the belt part 41 is adjusted to loosen the belt main body part 43 between the engaging member 50 and the device 20. Next, using the rotation assisting tool 210, the rotating part 62 which has been rotated to turn the long direction LD of the locking member 60 to extend along the short direction (Y direction) of the hole 30 is rotated by 90 degrees toward the long direction (X direction) of the hole 30. Accordingly, since the rotating part 62 returns to the state in which the long direction LD of the rotating part 62 extends along the long direction (X direction) of the hole 30 in a plan view, the locking member 60 inserted together with a part of the belt main body part 43 into the hole 30 may be removed from the hole 30.

Effect of First Embodiment

As described above, the first embodiment provides the locking member 60 which locks a part of the belt 40 holding the device 20 to the hole 30 formed in the bottom member 11. Accordingly, since a part of the belt 40 holding the device 20 is locked to the hole 30 formed in the bottom member 11, the device 20 can be fixed on the bottom member 11 by the locked belt 40. Therefore, since the arrangement position of the device 20 is not limited to, for example, inside of the hole 30 formed in the bottom member 11, the device 20 may be arranged on the bottom member 11 at a position other than in the hole 30. Further, since the device 20 is not arranged in the hole 30 formed in the bottom member 11, a device 20 having a size larger than the size of the hole 30 may be arranged on the bottom member 11. As a result, it is possible to arrange the device 20 on the bottom member 11 while suppressing restrictions on the arrangement position of the device 20 and the size of the device 20. Further, the belt 40 includes an end part provided with the engaging member 50 engageable with the edge part of the bottom member 11 or the frame 12. Accordingly, since the engaging member 50 can be engaged with the edge part of the bottom member 11 or the frame 12, the device 20 held by the belt 40 can be arranged at a desired position on the bottom member 11. Further, the belt 40 is not only engaged with the edge part of the bottom member 11 or the frame 12 by the engaging member 50, but the belt 40 is also locked to the hole 30 of the bottom member 11 by the locking member 60. Accordingly, the belt 40 can be locked more firmly than when the belt 40 is engaged only by the engaging member 50. Therefore, it is possible to suppress a position deviation of the device with respect to the bed-resting person resulting from back raising or foot raising (external force generated on the base) due to the raising function. As a result, it is possible to arrange the device 20 on the bottom member 11 while suppressing restrictions on the arrangement position of the device 20 and the size of the device 20, and meanwhile, it is also possible to suppress a position deviation of the device 20.

Further, in the first embodiment, as described above, the locking member 60 is configured to be inserted into the hole 30 from the upper surface side of the bottom member 11 toward the lower surface side of the bottom member 11 to lock a part of the belt 40 to the hole 30. Accordingly, since the belt 40 contacts (abuts against) the edge part of the hole 30 in a bent state at a portion where the upper edge part of the hole 30 of the bottom member 11 and the lower surface of the belt 40 are in contact with each other, a large frictional force is generated at the contact portion. Due to the frictional force, the belt 40 can be appropriately fixed to the hole 30 without deviation. Therefore, it is possible to appropriately suppress a position deviation of the device 20 with respect to the bed-resting person resulting from back raising or foot raising due to the raising function.

Further, in the first embodiment, as described above, the locking member 60 is configured to lock a part of the belt 40 on the lower surface of the bottom member 11 by inserting into the hole 30 together with the part of the belt 40. Accordingly, with the locking member 60 preventing the belt 40 from coming off from the hole 30, the belt 40 inserted into the hole 30 can be fixed more appropriately.

Further, in the first embodiment, as described above, the locking member 60 is configured to include a plate-shaped member having an elongated shape and is engaged with the bottom member 11 by arranging the long direction LD of the locking member 60 toward the short direction (Y direction) of the hole 30 on the lower surface of the bottom member 11 to be capable of preventing coming off from the hole 30 together with the belt 40. Accordingly, by having the locking member 60 pulled against the lower surface of the bottom member 11, the locking member 60 can be appropriately fixed to the hole 30. Therefore, the belt 40 inserted into the hole together with the locking member 60 can be more appropriately fixed.

Further, in the first embodiment, as described above, the locking member 60 includes the rotating part 62 which is rotatable and has a plate-shaped member having an elongated shape, and in a state in which the rotating part 62 inserted into the hole 30 from the upper surface side of the bottom member 11 with the long direction LD of the locking member 60 extending along the long direction (X direction) of the hole 30 is rotated toward the short direction (Y direction) of the hole 30 on the lower surface of the bottom member 11, a part of the rotating part 62 is engaged with the bottom member 11. Accordingly, by rotating the rotating part 62 inserted into the hole 30, the locking member 60 can be easily abutted against the lower surface of the bottom member 11. Therefore, the belt 40 inserted into the hole together with the locking member 60 can be more appropriately fixed.

Further, in the first embodiment, as described above, the locking member 60 includes the clipping part 61 which clips a part of the belt 40 and the rotating part 62 which has a plate-shaped member having an elongated shape and is rotatable with respect to the clipping part 61, and in a state in which the rotating part 62 inserted into the hole 30 from the upper surface side of the bottom member 11 with the long direction LD of the locking member 60 extending along the long direction (X direction) of the hole 30 is rotated toward the short direction (Y direction) of the hole 30 on the lower surface of the bottom member 11, a part of the rotating part 62 is engaged with the bottom member 11. Accordingly, by rotating the rotating part 62 inserted into the hole 30, the locking member 60 can be easily abutted against the lower surface of the bottom member 11. Therefore, the belt 40 inserted into the hole together with the locking member 60 can be more appropriately fixed.

Further, in the first embodiment, as described above, the plate-shaped member of the locking member 60 is configured to have a rectangular shape having a long edge and a short edge in a plan view. Accordingly, the two end parts of the long direction of the plate-shaped member or the rod-shaped member of the locking member 60 can be easily engaged with the lower surface of the bottom member 11.

Further, in the first embodiment, as described above, the belt 40 is composed of the pair of belt parts 41 connected to one side and the other side of the device 20, and the pair of belt parts 41 each includes the engaging member 50, the connecting part 42 connectable with the device 20, and the belt main body part 43 connecting the engaging member 50 and the connecting part 42. Accordingly, with the connecting parts 42 of the pair of belt parts 41, the device 20 can be appropriately held from one side and the other side of the device 20 even at a position where the hole 30 is not provided.

Further, as described above, the first embodiment includes the rotation assisting tool 210 and the device holding member 100, and the device holding member 100 is attached to the bed 10 including the bottom member 11 formed with the holes 30 and the frame 12 supporting the bottom member 11, and holds the device 20 arranged on the bottom member 11. The rotating part 62 includes multiple recesses 64 provided on one side and the other side of the rotation center axis on the upper surface, and the rotation assisting tool 210 includes multiple protrusions 212 provided in correspondence to the recesses 64 of the rotating part 62. Accordingly, the rotating part 62 can be rotated by the rotation assisting tool 210.

Further, in the first embodiment, as described above, with the protrusions 212 of the rotation assisting tool 210 inserted into the recesses 64 of the rotating part 62, the rotating part 62 is rotatable by rotating the rotation assisting tool 210 around the rotation center axis. Accordingly, the rotating part 62 can be easily rotated by the rotation assisting tool 210.

Second Embodiment

Next, referring to FIG. 16 to FIG. 20, the configuration of the device holding member 100 according to a second embodiment will be described. In the first embodiment described above, the holes 30 formed in the bottom member 11 are arranged so that the long edge of the hole 30 extends along in the left-right direction of the bed 10, and the rotating part 62 is configured to have a rectangular shape having a long edge and a short edge in a plan view. Different from the first embodiment, in the second embodiment, the holes 30 formed in the bottom member 11 are arranged so that the short edge of the hole 30 extends along the left-right direction of the bed 10, a rotating part 72 includes a pair of long edges 76 and notched parts 75 cut out respectively at the pair of long edges 76 in a plan view, and with a locking member 70 engaged with the bottom member 11 on the lower surface of the bottom member 11, a part of the belt 40 is arranged in the notched part 75.

(Configuration of Holes Formed in Bottom Member)

Figure 16:
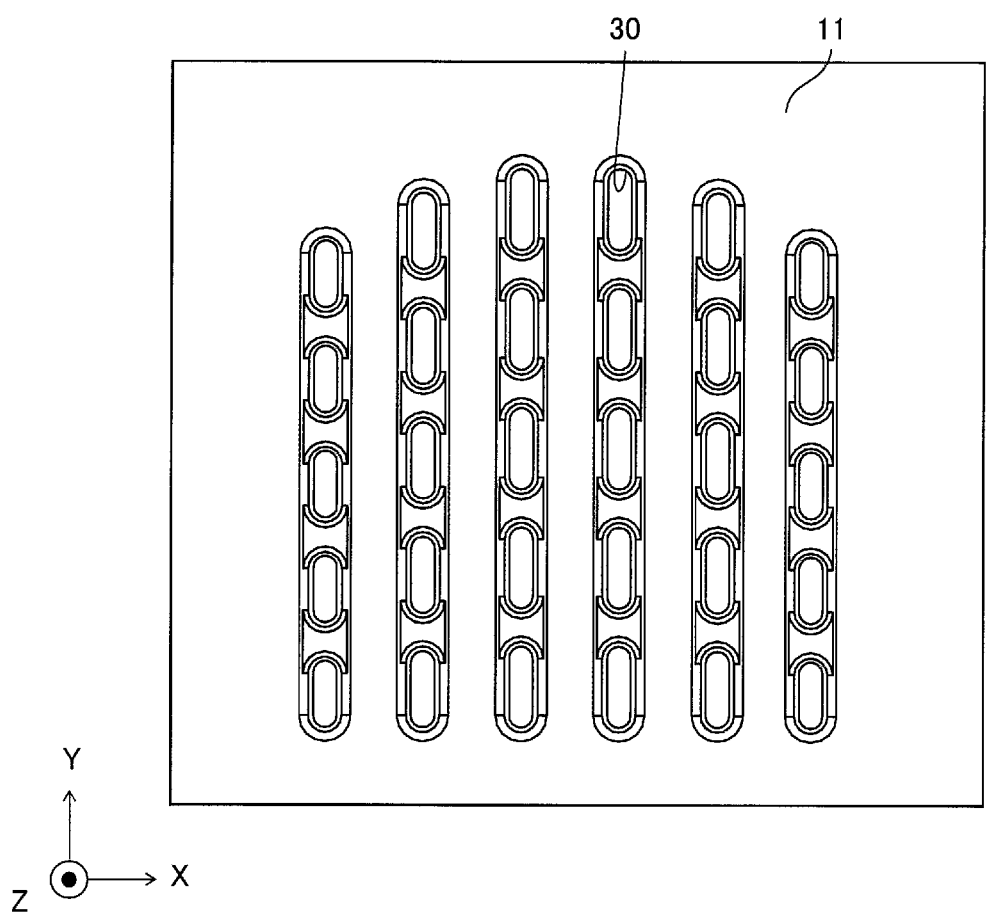
FIG. 16 is a schematic view showing an example of a hole formed in the bottom member according to a second embodiment.

As shown in FIG. 16, the holes 30 formed in the bottom member 11 have an elliptical shape having a long axis and a short axis in a plan view. The holes 30 are arranged so that the short axis of the hole 30 extends along the left-right direction (Y direction) of the bed 10.

(Configuration of Rotating Part)

Figure 17:
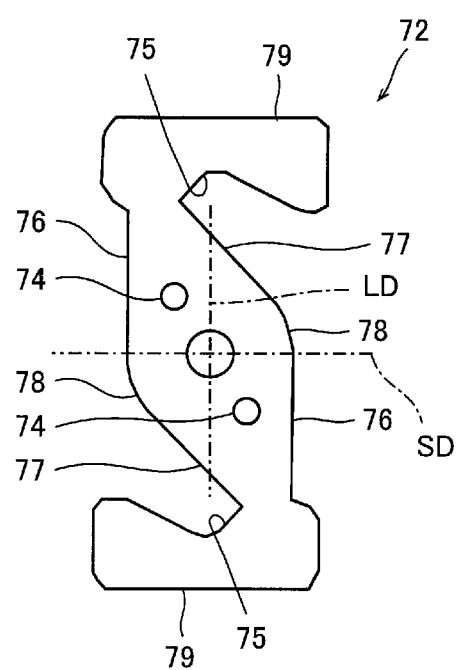
FIG. 17 is a schematic plan view of a rotating part in a locking member according to the second embodiment.

As shown in FIG. 17, the rotating part 72 includes a pair of long edges 76 and a pair of notched parts 75 cut out respectively at the pair of long edges in a plan view. Each of the notched parts 75 is cut toward a short edge 79 close to the position where the notched part 75 is formed at the long edge 76. The pair of notched parts 75 is respectively arranged on one side and the other side of a shaft part 73 (see FIG. 18). The end part of the notched part 75 on the shaft part 73 side includes a straight part 77 in a plan view. The straight part 77 in the notched part 75 and each of the pair of long edges 76 are connected by a curve part 78 which is curved. Since the configurations of a clipping part 71 (see FIG. 18) and the shaft part 73 are the same as the configurations of the clipping part of the locking member and the shaft part according to the first embodiment, the descriptions thereof will be omitted.

(Method of Locking Belt Main Body Part by Locking Member)

Figure 18:
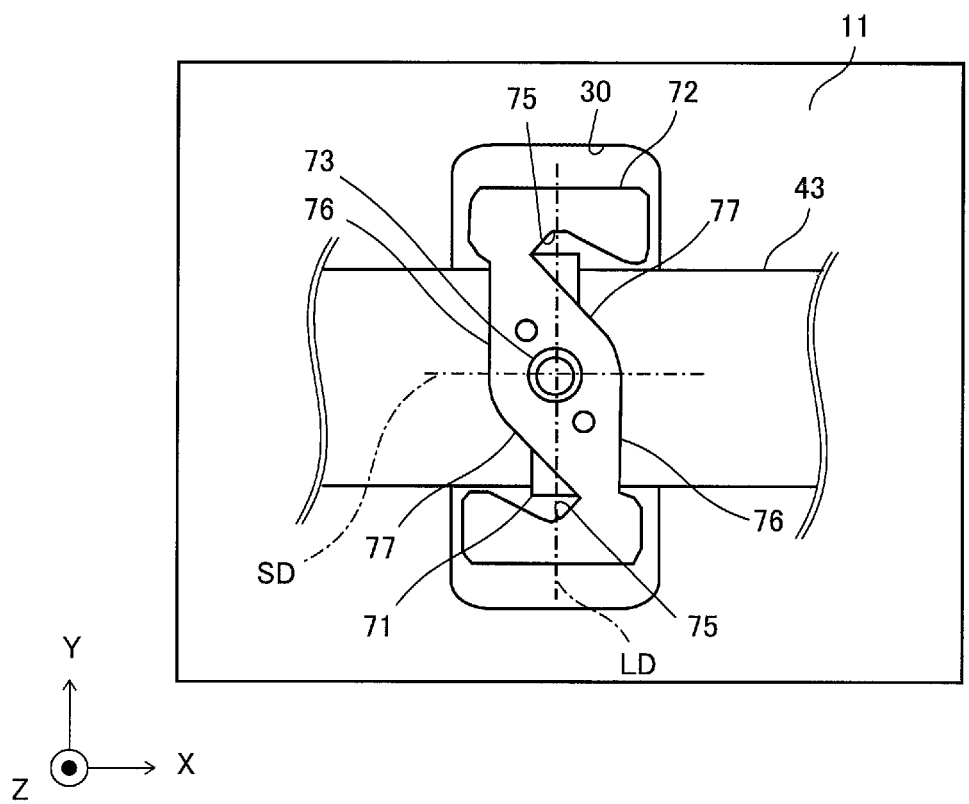
FIG. 18 is a first view showing a locking method by the locking member according to the second embodiment.
Figure 19:
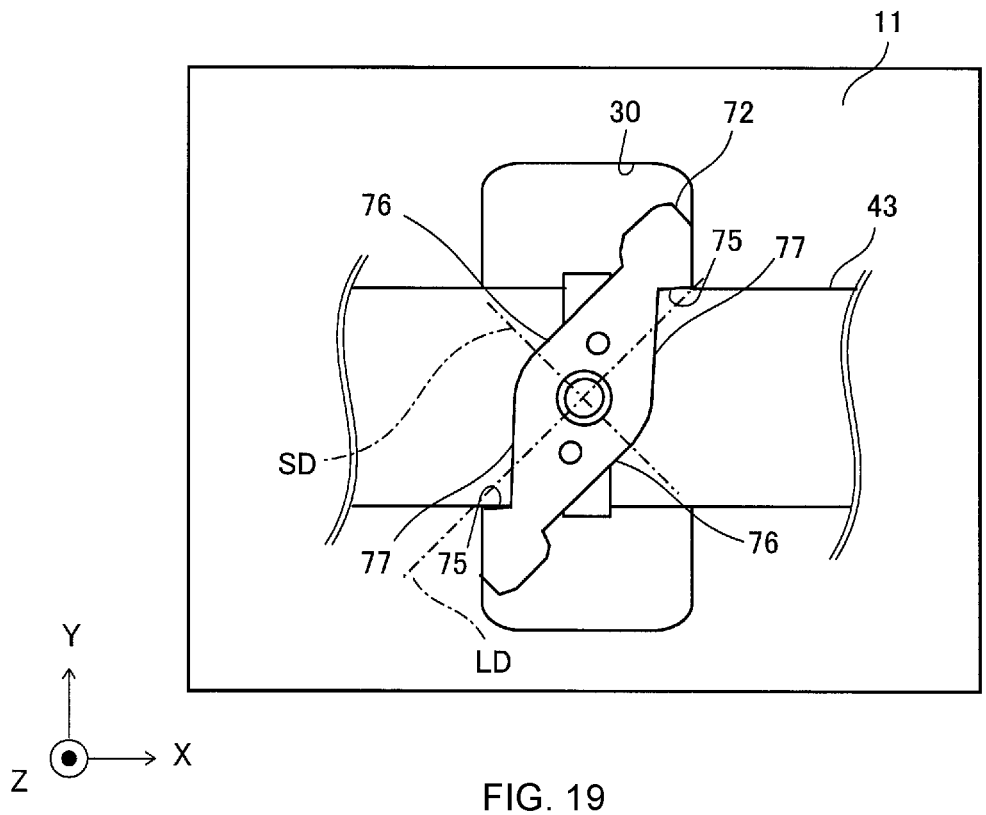
FIG. 19 is a second view showing the locking method by the locking member according to the second embodiment.
Figure 20:
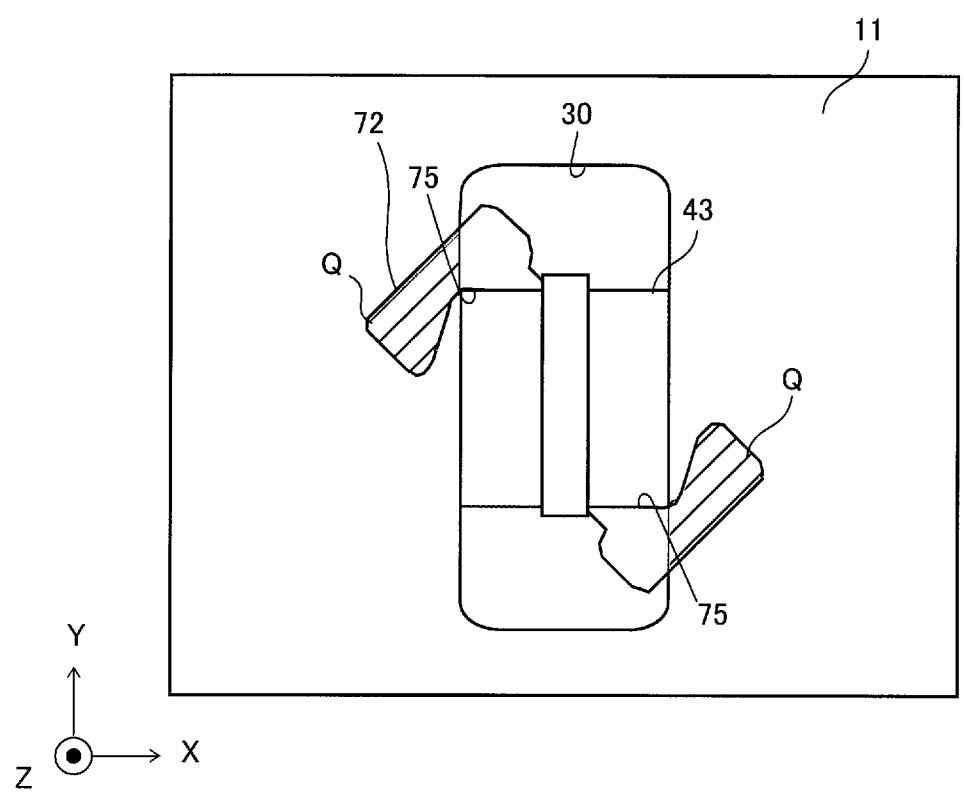
FIG. 20 is a third view showing the locking method by the locking member according to the second embodiment.

Referring to FIG. 18 to FIG. 20, a method of locking the belt main body part 43 by the locking member 70 according to the second embodiment will be described.

FIG. 18 is a schematic view showing a state in which the locking member 70 is inserted into the hole 30 formed in the bottom member 11 as viewed from the upper surface side of the bottom member 11. As shown in FIG. 18, the belt main body part 43 is placed so that the long direction of the belt main body part 43 extends along the short direction (X direction) of the hole 30, and the belt main body part 43 passes over the hole 30. The clipping part 71 clips the belt main body part 43. The rotating part 72 is arranged to be accommodated in the hole 30 with the long direction LD of the rotating part 72 extending along the long direction (Y direction) of the hole 30. In a plan view, a part of the end part of the short direction of the belt main body part 43 is arranged to overlap in the notched part 75. The locking member 70 is inserted together with a part of the belt main body part 43 into the hole 30 from the upper surface side of the bottom member 11 toward the lower surface side of the bottom member 11. In the hole 30, the upper surface of the rotating part 72 is inserted to be located lower than the lower surface of the bottom member 11.

FIG. 19 is a schematic view showing a state in which the rotating part 72 of FIG. 18 is rotated as viewed from the upper surface side of the bottom member 11. FIG. 20 is a schematic view showing a state in which the rotating part 72 of FIG. 18 is rotated as viewed from the lower surface side of the bottom member 11. FIG. 19 and FIG. 20 show a state in which the rotating part 72 inserted into the hole 30 with the long direction LD of the locking member 70 extending along the long direction (Y direction) of the hole 30 as shown in FIG. 18 is rotated by 45 degrees toward the short direction (X direction) of the hole 30 on the lower surface of the bottom member 11. In other words, the locking member 70 inserted into the hole 30 with the long direction LD of the locking member 70 extending along the long direction (Y direction) of the hole 30 is arranged to be tilted by 45 degrees toward the short direction (X direction) of the hole 30 on the lower surface of the bottom member 11. A part of the end part of the short direction of the belt main body part 43 is arranged in the notched part 75. The rotation of the rotating part 72 is performed by using the rotation assisting tool 210.

After the rotating part 72 is rotated, by adjusting the adjuster 44 of the belt part 41 to apply a tension to the belt main body part 43 between the engaging member 50 and the device 20, as shown in FIG. 19 and FIG. 20, the upper surface at a vicinity Q (hatched portion in FIG. 20) near the notched part 75 of two end parts of the long direction LD of the rotating part 72 abuts against the lower surface of the bottom member 11. Accordingly, by having the vicinity Q of the two end parts of the long direction LD of the rotating part 72 pulled against the lower surface of the bottom member 11, the rotating part 72 and the bottom member 11 are engaged with each other, and as a result, the locking member 70 prevents coming off from the hole 30 together with the belt main body part 43. In addition, with the upper surface at the vicinity Q of the notched part 75 of the rotating part 72 abutted against the lower surface of the bottom member 11, the straight part 77 of the notched part 75 and the belt main body part 43 abut against each other, and the bottom member 11 on the long edge side of the hole 30 and the belt main body part 43 abut against each other. Accordingly, a frictional force is generated between the vicinity of the straight part 77 of the notched part 75 of the rotating part 72 and the belt main body part 43 that abuts against the vicinity of the straight part 77, and a frictional force is also generated between the bottom member 11 on the long edge side of the hole 30 and the belt main body part 43 that abuts against the bottom member 11. Therefore, the belt main body part 43 is less likely to deviate with respect to the hole 30, and as a result, the belt main body part 43 is locked to the hole 30.

Other configurations of the second embodiment are the same as those of the first embodiment.

Effect of Second Embodiment

In the second embodiment, as described above, the plate-shaped member or the rod-shaped member of the locking member 70 includes the pair of long edges 76 and the notched parts 75 cut out respectively at the pair of long edges 76 in a plan view, and with the locking member 70 engaged with the bottom member 11 on the lower surface of the bottom member 11, a part of the belt 40 is arranged in the notched part 75. Accordingly, the two end parts of the long direction of the plate-shaped member or the rod-shaped member of the locking member 70 and the lower surface of the bottom member 11 can be appropriately engaged with each other, and in the notched part 75, a part of the belt 40 can also be locked by the notched part 75 and the bottom member 11.

Moreover, other effects of the second embodiment are the same as those of the first embodiment.

Third Embodiment

Next, referring to FIG. 21 to FIG. 24, the configuration of the device holding member 100 according to a third embodiment will be described. Different from the first embodiment in which the locking member 60 includes the clipping part 61, the rotating part 62, and the shaft part 63, in the third embodiment, a locking member 80 is configured to include a pair of sidewalls 81 and a bottom part 82 connecting the pair of sidewalls 81.

(Configuration of Locking Member)

Figure 21:
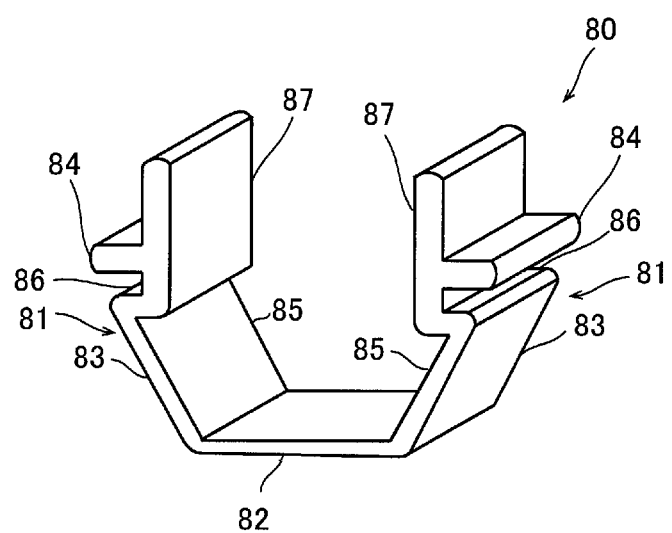
FIG. 21 is a perspective view of a locking member according to a third embodiment.

As shown in FIG. 21, the locking member 80 according to the third embodiment includes a pair of sidewalls 81 and a bottom part 82 connecting the pair of sidewalls 81. The locking member 80 is formed of a material allowing elastic deformation of the pair of sidewalls 81 in a direction approaching each other. The material of the locking member 80 may be the same as or different from the material of the locking members 60 and 70 in the first embodiment and the second embodiment.

The pair of sidewalls 81 includes a pair of wall parts 83 connected to the bottom part 82 and at least one pair of protruding parts 84 protruding from the pair of wall parts 83 toward an outer side of the pair of wall parts. The pair of wall parts 83 is configured to include a first portion 85, a second portion 86, and a third portion 87 from one end connected to the bottom part 82 toward the other end. The first portion 85 is configured so that a distance between the pair of wall parts 83 increases toward the other end side. The second portion 86 is configured to connect the first portion 85 and the third portion 87 and protrude inward in the pair of wall parts 83. The third portion 87 is configured to extend toward a side opposite to the bottom part 82 side. The at least one pair of protruding parts 84 is formed at the third portion 87. The amount of outward protrusion of the first portion 85 is configured to be smaller than the amount of outward protrusion of the pair of protruding parts 84 that is closest to the first portion 85. In the third embodiment, the protruding parts 84 are formed in one pair. The bottom part 82 is configured to connect the pair of sidewalls 81.

(Method of Locking Belt Main Body Part by Locking Member)

Figure 22:
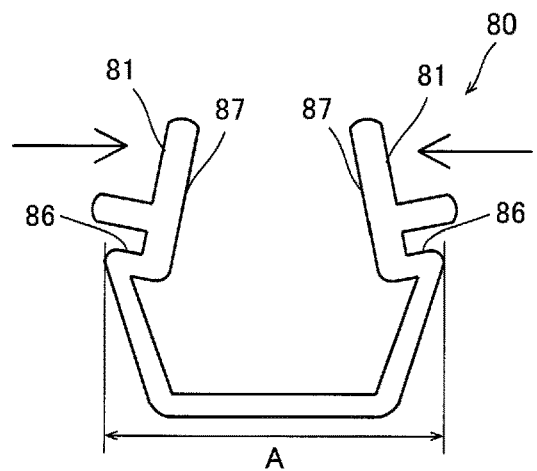
FIG. 22 is a first view showing a locking method by the locking member according to the third embodiment.
Figure 23:
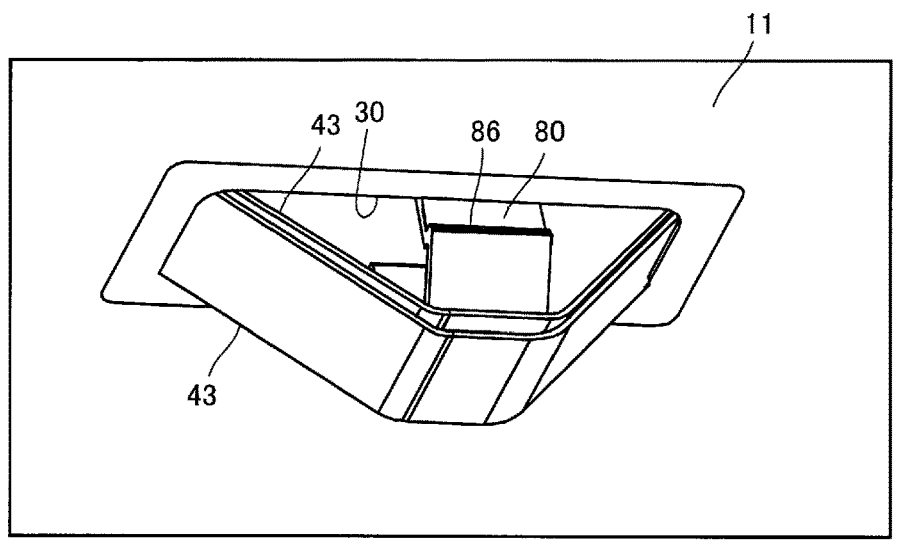
FIG. 23 is a second view showing the locking method by the locking member according to the third embodiment.
Figure 24:
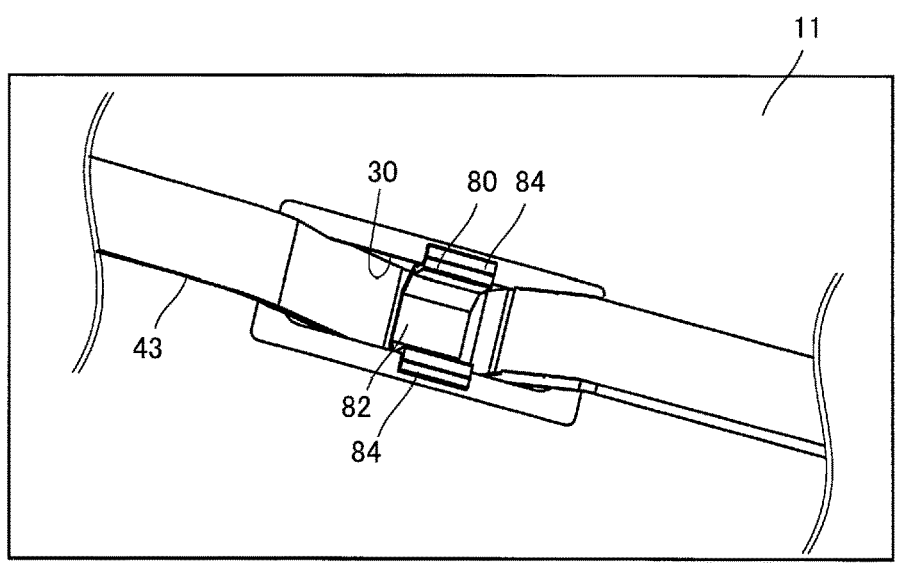
FIG. 24 is a third view showing the locking method by the locking member according to the third embodiment.

Referring to FIG. 22 to FIG. 24, a method of locking the belt main body part 43 by the locking member 80 according to the third embodiment will be described.

First, the belt 40 which holds the device 20 is placed on the bottom member 11 with the long direction of the belt main body part 43 extending along the left-right direction of the bed 10, and a part of the belt main body part 43 inserted into the hole 30 formed in the bottom member 11. In this state in which the belt 40 is placed, as shown in FIG. 22, the locking member 80 is elastically deformed inward by pressing the third portions 87 of the pair of sidewalls 81 with fingers in a direction in which the pair of sidewalls 81 approaches each other. Accordingly, a distance A between the outer surfaces of the second portions 86 of the pair of sidewalls 81 becomes smaller than that before the elastic deformation.

As shown in FIG. 23, the direction in which the pair of sidewalls 81 approaches each other is aligned with the short direction of the belt main body part 43 inserted into the hole 30, and the elastically deformed locking member 80 is inserted into the hole 30 from the bottom part 82 side. The locking member 80 inserted into the hole 30 is restored by releasing the pressing of the fingers. As a result, as shown in FIG. 23 and FIG. 24, with the pair of sidewalls 81 restored, the bottom member 11 is clipped between the pair of protruding parts 84 and the second portions 86. After the pair of sidewalls 81 is restored, by adjusting the adjuster 44 of the belt part 41 to apply a tension to the belt main body part 43 between the engaging member 50 and the device 20, a part of the belt main body part 43 abuts against the lower surface of the bottom part 82.

By clipping the bottom member 11 between the pair of protruding parts 84 and the second portions 86, the pair of protruding parts 84 and the bottom member 11 are engaged, and as a result, the locking member 80 prevents coming off from the hole 30 together with the belt main body part 43. Further, with the bottom member 11 clipped between the pair of protruding parts 84 and the second portions 86, the bottom member 11 in the left-right direction of the hole 30 and the belt main body part 43 abut against each other. Accordingly, a frictional force is generated between the bottom member 11 in the left-right direction of the hole 30 and the belt main body part 43 that abuts against the bottom member 11. Therefore, the belt main body part 43 is less likely to deviate with respect to the hole 30, and as a result, the belt main body part 43 is locked to the hole 30.

A method of releasing locking of the belt main body part 43 to the hole by the locking member 80 and pulling the locking member 80 out of the hole 30 will be described. With a part of the belt main body part 43 locked to the hole 30 by the locking member 80, while pressing the third portions 87 of the pair of sidewalls 81 with fingers in a direction in which the pair of sidewalls 81 approaches each other, the pair of sidewalls 81 is tilted to pull one of the first portions 85 of the pair of sidewalls 81 out of the hole 30. Since the amount of outward protrusion of the first portions 85 of the pair of sidewalls 81 is configured to be smaller than the amount of outward protrusion of the pair of protruding parts 84, the one of the first portions 85 of the pair of sidewalls 81 can be pulled out of the hole 30. By pulling the one of the first portions 85 of the pair of sidewalls 81 out of the hole 30, the other of the first portions 85 can also be pulled out of the hole 30. Accordingly, the locking member 80 inserted together with a part of the belt main body part 43 into the hole 30 can be pulled out of the hole 30.

Other configurations of the third embodiment are the same as those of the first embodiment.

Effect of Third Embodiment

In the third embodiment, as described above, the locking member 80 includes the pair of sidewalls 81 and the bottom part 82 connecting the pair of sidewalls 81, and by restoring the pair of sidewalls 81 which has been inserted into the hole 30 from the bottom part 82 side with the pair of sidewalls 81 elastically deformed in a direction approaching each other, the locking member 80 can prevent coming off from the hole 30 together with the belt 40. Accordingly, the locking member 80 can be easily inserted into the hole 30 from the upper surface side of the bottom member 11, and the restored locking member 80 and the bottom member 11 can be easily engaged with each other. Therefore, the belt 40 inserted into the hole 30 together with the locking member 80 can be more appropriately fixed.

Further, in the third embodiment, as described above, the locking member 80 includes the pair of sidewalls 81 and the bottom part 82 connecting the pair of sidewalls 81, and the pair of sidewalls 81 includes a pair of wall parts 83 connected to the bottom part 82 and at least one pair of protruding parts 84 protruding from the pair of wall parts 83 toward an outer side of the pair of wall parts 83. With restoration of the pair of sidewalls 81 which has been inserted into the hole 30 from the bottom part 82 side with the pair of sidewalls 81 elastically deformed in the direction approaching each other, the pair of protruding parts 84 is engaged with the end parts of the hole 30. Accordingly, the locking member 80 can be easily inserted into the hole 30 from the upper surface side of the bottom member 11, and the pair of protruding parts 84 of the restored locking member 80 and the bottom member 11 can also be easily engaged with each other. Therefore, the belt 40 inserted into the hole 30 together with the locking member 80 can be more appropriately fixed.

Modification Examples

The embodiments disclosed herein are exemplary in all respects and are not considered to be restrictive. The scope of the disclosure is shown by the claims rather than the descriptions of the embodiments above, and further includes all changes (modification examples) within the equivalents of the claims.

For example, the first embodiment to the third embodiment have shown an example in which the base is the bottom member 11 included in the bed 10, but the disclosure is not limited thereto. The base may be, for example, provided inside an ambulance and mounted with a medical device, and may be composed of a member having holes formed for weight reduction. Even in that case, it is possible to arrange the device on the base while suppressing restrictions on the arrangement position of the device and the size of the device, and meanwhile, it is also possible to suppress a position deviation of the device 20 resulting from an external force such as vibration generated on the base during travel. The base is, for example, a member having at least one plane on which a through-hole is formed.

Figure 25:
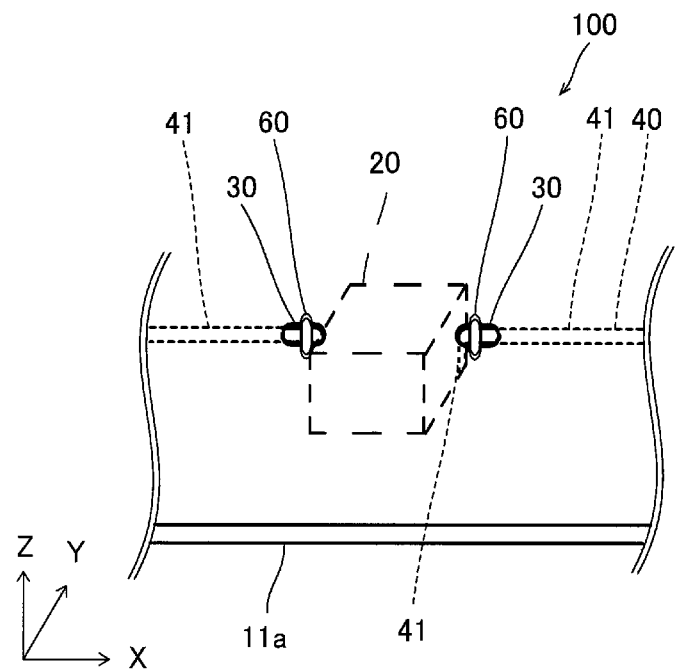
FIG. 25 is a first view showing arrangement of a device on a base according to a modification example.
Figure 26:
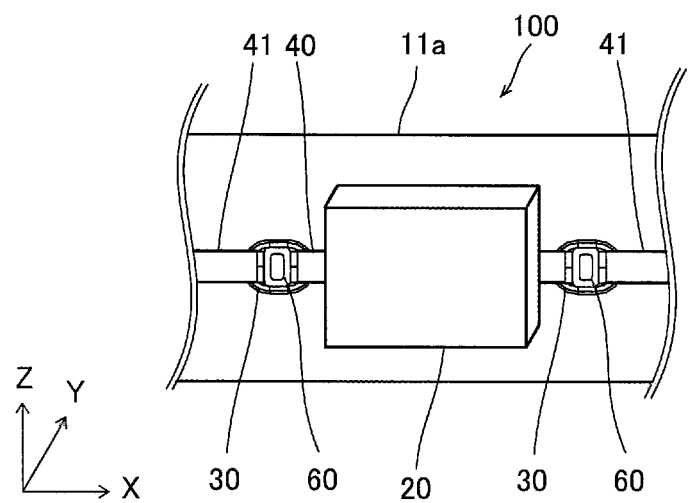
FIG. 26 is a second view showing arrangement of a device on a base according to a modification example.

Further, the first embodiment to the third embodiment described above have shown an example in which the device 20 is arranged on the upper surface of the bottom member 11 which is an example of the base, and the locking member 60 is inserted together with a part of the belt main body part 43 into the hole 30 from the upper surface side of the bottom member 11 toward the lower surface side of the bottom member 11, but the disclosure is not limited thereto. For example, as shown in FIG. 25, the device 20 may be arranged on the lower surface of a base 11a, and the locking member 60 may be inserted together with a part of the belt main body part 43 into the hole 30 from the lower surface side of the base 11a toward the upper surface side of the base 11a. Further, as shown in FIG. 26, the device 20 may be arranged on a surface along the vertical direction of the base 11a, and the locking member 60 may be inserted together with a part of the belt main body part 43 into a hole 30 formed on the surface along the vertical direction from a side of a surface in one direction of the base 11a toward a side of a surface in another direction of the base 11a.

Further, the first embodiment to the third embodiment described above have shown an example in which the belt 40 is composed of the pair of belt parts 41 connected to one side and the other side of the device 20, but the disclosure is not limited thereto. For example, the belt 40 may be composed of one belt part 41 including the engaging members 50 provided at two end parts and the belt main body part 43 connecting the engaging members 50, and may include a connecting part connecting the device 20 to the belt main body part 43.

Figure 27:
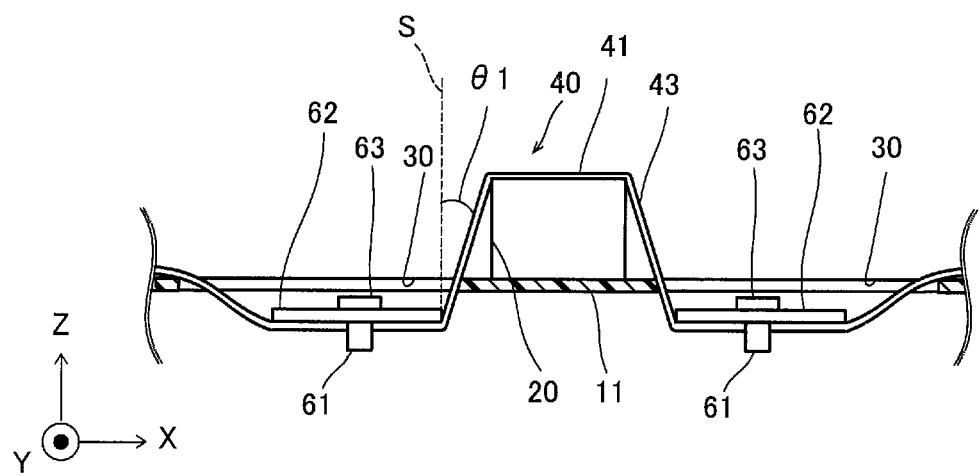
FIG. 27 is a cross-sectional view showing a method of holding a device by a device holding member according to a modification example.

Further, as shown in FIG. 27, when the belt 40 is composed of one belt part 41 including the engaging members 50 provided at two end parts and the belt main body part 43 connecting the engaging members 50, the upper surface of the device 20 may be pressed by the lower surface of the belt part 41 without a connecting part connecting the device 20 to the belt main body part 43. In that case, an angle θ1 formed by a normal direction S of the bottom member 11, which is an example of the base, and the belt main body part 43 is an acute angle, and the device 20 is arranged with respect to the position of the hole 30 so that the angle becomes smaller. Accordingly, since the force of pressing the device 20 toward the bottom member 11 by the belt 40 increases, the frictional force at the portion where the device 20 and the bottom member 11 are in contact with each other increases. Therefore, a position deviation of the device 20 can be further suppressed. Further, to arrange the device 20 with respect to the position of the hole 30 so that the angle θ1 becomes smaller, for example, among the holes 30 formed in the bottom member 11, the belt main body part 43 may be locked to a hole 30 closer to the device 20 by the locking member 60. Further, when the belt 40 is composed of one belt part 41 including the engaging members 50 provided at two end parts and the belt main body part 43 connecting the engaging members 50, the belt part 41 may be inserted into insertion holes provided on the lower surface side of the device 20 and formed in the left-right direction of the device 20 without a connecting part connecting the device 20 to the belt main body part 43.

Further, the first embodiment to the third embodiment have shown an example in which the length of the belt 40 is adjustable by the adjuster 44 provided at the belt main body part 43, but the disclosure is not limited thereto. The length of the belt 40 may also be adjustable by either the engaging member 50 or the connecting part 42. For example, the engaging member 50 may be a hook attached with an adjuster which can slidably adjust the length of a part of the hook. Alternatively, the connecting part 42 may be composed of an engaging member which is engageable with the device 20 and attached with an adjuster that can slidably adjust the length.

Further, the first embodiment to the third embodiment described above have shown an example in which the connecting part 42 is configured to hold the device 20 by folding back the belt main body part 43 formed of a band-shaped member in the insertion hole provided at the device 20, but the disclosure is not limited thereto. The connecting part 42 may also be composed of a member engageable with an engaging part provided at the device 20.

Figure 28:
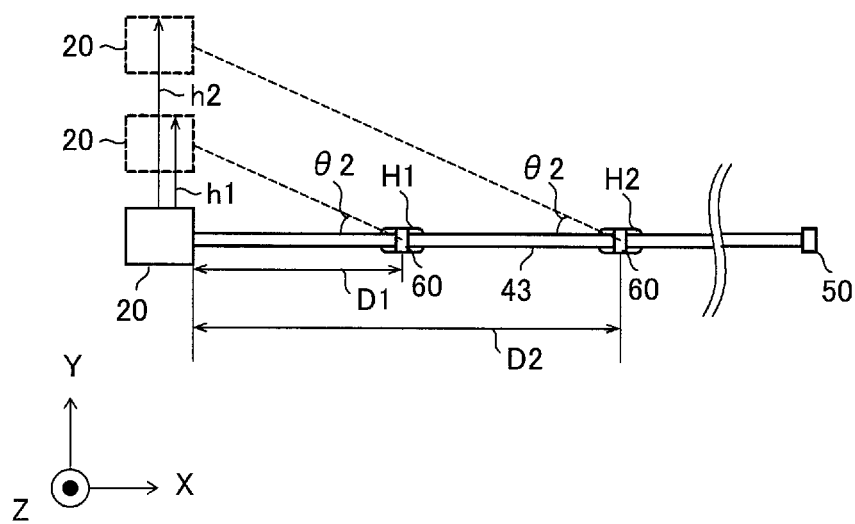
FIG. 28 is a schematic view showing a relationship between the distance between the hole and the device and the position deviation amount of the device.

Further, the first embodiment to the third embodiment described above have shown an example in which among the holes 30 formed in the bottom member 11, the position of the hole into which the locking member 60 is inserted is not particularly limited, but the disclosure is not limited thereto. Even if the adjuster 44 of the belt part 41 is used for adjustment so that a tension is applied to the belt main body part 43 between the engaging member 50 and the device 20, a slight loosening (amount of play) of the belt main body part 43 may occur between the engaging member 50 and the device 20. Due to this loosening, the device 20 may deviate in the head-foot direction of the bed 10 at the time of back raising or foot raising. At this time, as shown in FIG. 28, when an angle θ2 formed by a straight line connecting between the hole 30 in which the belt main body part 43 is locked by the locking member 60 and the position of the device 20 is the same before and after back raising or foot raising, a deviation amount h1 with a hole H1 which is at a distance D1 from the device 20 is smaller than a deviation amount h2 with the hole H2 which is at a distance D2 from the device 20 larger than the distance D1. Accordingly, among the holes 30 formed in the bottom member 11 along the left-right direction of the bed 10, by locking the belt main body part 43 to the hole 30 closer to the device 20 by the locking member 60, it is possible to suppress a position deviation of the device resulting from an external force such as back raising or foot raising due to the raising function.

Therefore, among the holes 30 formed in the bottom member 11, the belt main body part 43 may be locked to the hole 30 closer to the device 20 by the locking member 60.

Further, the first embodiment has shown an example in which the rotating part 62 is rotated by 90 degrees toward the short direction of the hole 30, and the second embodiment has shown an example in which the rotating part 72 is rotated by 45 degrees toward the short direction of the hole 30, but the disclosure is not limited thereto. The angle by which the rotating parts 62 and 72 are rotated toward the short direction of the hole 30 is not particularly limited as long as a part of the rotating parts 62 and 72 can be engaged with the bottom member 11.

Further, the first embodiment and the second embodiment have shown an example in which the material of the clipping parts 61 and 71 is not particularly limited, but the disclosure is not limited thereto. After the rotating parts 62 and 72 are rotated, the adjuster 44 of the belt part 41 is adjusted to facilitate application of a tension to the belt main body part 43 between the engaging member 50 and the device 20, so the clipping parts 61 and 71 may be made of a material in which a frictional force generated between the clipping parts 61 and 71 and the belt main body part 43 on the surface in contact with the belt main body part 43 is relatively small. Further, a processing may be applied to reduce the frictional force generated between the clipping parts 61 and 71 and the belt main body part 43. Further, in the third embodiment, after the pair of sidewalls 81 inserted into the hole 30 is restored, the adjuster 44 of the belt part 41 is adjusted to facilitate application of a tension to the belt main body part 43 between the engaging member 50 and the device 20, so a processing may be performed on the surface of the bottom part 82 in contact with the belt main body part 43 to reduce the frictional force generated between the bottom part 82 and the belt main body part 43.

Further, the third embodiment has shown an example in which the pair of protruding parts 84 is one pair, but the disclosure is not limited thereto. To make it less slippery for the fingers when holding the pair of sidewalls 81 with the fingers, multiple pairs of protruding parts 84 may be provided, or a processing may be performed to increase the frictional force of the third portion 87 of the pair of sidewalls 81.

Further, the first embodiment to the third embodiment described above have shown an example in which the belt main body part 43 is inserted into the hole 30, and the locking members 60, 70, and 80 are also inserted into the hole 30, but the disclosure is not limited thereto. For example, the locking member may include a clip that is locked to the hole 30.

Further, the first embodiment has shown an example in which the grip part 211 of the rotation assisting tool 210 has a rectangular parallelepiped shape, but the disclosure is not limited thereto. The shape of the grip part 211 is not particularly limited as long as it can be gripped by the fingers of a hand and is in a shape that is easy to rotate.

Further, the first embodiment has shown an example in which the rotating part 62 is rotated by using the rotation assisting tool 210, but the disclosure is not limited thereto. For example, the rotating part 62 may include a protruding part on the upper surface that can be pinched with the fingers, and by rotating the protruding part on the axis of the shaft part 63, the rotating part 62 may be rotatable.

Further, the first embodiment to the third embodiment have shown an example in which the belt part 41 includes the belt main body part 43, but the disclosure is not limited thereto. For example, the belt main body part 43 may be composed of a belt or a rope made of a polyester or nylon material, or may be composed of a belt or a band made of a nitrile rubber or natural rubber.

What is claimed is:

1. A device holding member which is engaged with a base formed with a hole or a frame supporting the base and holds a device arranged on the base, the device holding member comprising:
    a belt which comprises an end part provided with an engaging member engageable with an edge part of the base or the frame and holds the device; and
    a locking member which is provided between the engaging member and the device and locks a part of the belt to the hole.

2. The device holding member according to claim 1, wherein the locking member is configured to be inserted into the hole from a side of a surface in one direction of the base to a side of a surface in another direction of the base to lock the part of the belt to the hole.

3. The device holding member according to claim 2, wherein the locking member is configured to lock the part of the belt on the surface in the another direction of the base by inserting into the hole together with the part of the belt.

4. The device holding member according to claim 3, wherein the locking member is configured to comprise a plate-shaped member or a rod-shaped member having an elongated shape, and
    the locking member is engaged with the base by arranging a long direction of the locking member toward a short direction of the hole on the surface in the another direction of the base to be capable of preventing coming off from the hole together with the belt.

5. The device holding member according to claim 1, wherein the locking member is configured to comprise a rotating part which is rotatable and has a plate-shaped member or a rod-shaped member having an elongated shape, and
    in a state in which the rotating part inserted into the hole from a side of a surface in one direction of the base with a long direction of the locking member extending along a long direction of the hole is rotated toward a short direction of the hole on a surface in another direction of the base, a part of the rotating part is engaged with the base.

6. The device holding member according to claim 1, wherein the locking member is configured to comprise a clipping part which clips the part of the belt and a rotating part which has a plate-shaped member or a rod-shaped member having an elongated shape and is rotatable with respect to the clipping part, and
    in a state in which the rotating part inserted into the hole from a side of a surface in one direction of the base with a long direction of the locking member extending along a long direction of the hole is rotated toward a short direction of the hole on a surface in another direction of the base, a part of the rotating part is engaged with the base.

7. The device holding member according to claim 4, wherein the plate-shaped member or the rod-shaped member of the locking member is configured to have a rectangular shape having a long edge and a short edge in a plan view.

8. The device holding member according to claim 4, wherein the plate-shaped member or the rod-shaped member of the locking member is configured to comprise a pair of long edges and notched parts cut out respectively at the pair of long edges in a plan view, and with the locking member engaged with the base on the surface in the another direction of the base, the part of the belt is arranged in the notched part.

9. The device holding member according to claim 3, wherein the locking member is configured to comprise a pair of sidewalls and a bottom part connecting the pair of sidewalls, and
by restoring the pair of sidewalls which has been inserted into the hole from a side of the bottom part with the pair of sidewalls elastically deformed in a direction approaching each other, the locking member is capable of preventing coming off from the hole together with the belt.

10. The device holding member according to claim 1, wherein the locking member is configured to comprise a pair of sidewalls and a bottom part connecting the pair of sidewalls,
the pair of sidewalls comprises a pair of wall parts connected to the bottom part, and at least one pair of protruding parts protruding from the pair of wall parts toward an outer side of the pair of wall parts, and
with restoration of the pair of sidewalls which has been inserted into the hole from a side of the bottom part with the pair of sidewalls elastically deformed in a direction approaching each other, the pair of protruding parts is engaged with end parts of the hole.

11. The device holding member according to claim 1, wherein the belt is composed of a pair of belt parts connected to one side and another side of the device, and
each of the pair of belt parts comprises the engaging member, a connecting part connectable with the device, and a belt main body part which connects the engaging member and the connecting part.

12. The device holding member according to claim 11, wherein a length of the belt is configured to be adjustable by at least one of the engaging member, the connecting part, and the belt main body part.

13. A device holding member set comprising a device holding member which is engaged with a base formed with a hole or a frame supporting the base and holds a device arranged on the base, and a rotation assisting tool, wherein
the device holding member comprises:
a belt which holds the device and comprises an end part provided with an engaging member engageable with an edge part of the base or the frame; and
a locking member which is provided between the engaging member and the device and locks a part of the belt to the hole,
the locking member comprises a rotating part which is rotatable and has a plate-shaped member or a rod-shaped member having an elongated shape, wherein in a state in which the rotating part inserted into the hole from a side of a surface in one direction of the base with a long direction of the locking member extending along a long direction of the hole is rotated toward a short direction of the hole on a surface in another direction of the base, a part of the rotating part is engaged with the base,
the rotating part comprises multiple recesses arranged on one surface on one side and another side of a rotation center axis, and
the rotation assisting tool comprises multiple protrusions provided in correspondence to the recesses of the rotating part.

14. The device holding member set according to claim 13, wherein with the protrusions of the rotation assisting tool inserted into the recesses of the rotating part, the rotating part is configured to be rotatable by rotating the rotation assisting tool around the rotation center axis.

* * * * *